(12) United States Patent
Mori et al.

(10) Patent No.: US 6,498,149 B1
(45) Date of Patent: Dec. 24, 2002

(54) NATURAL ANTITUMOR OR ANTIVIRAL SUBSTANCES AND USE OF THE SAME

(75) Inventors: Tsuneatsu Mori, 17-2-501, Minami-Magome 5-Chome, Ota-Ku, Tokyo-To (JP); Maowu Guo, Lachine (CA); Etsuko Mori, Tokyo-To (JP)

(73) Assignees: Tsuneatsu Mori, Tokyo-to (JP); Takahide Mori, Kyoto (JP); Techno Seven Co., Ltd., Tokyo-to (JP)

( * ) Notice: Subject to any disclaimer, the term of this patent is extended or adjusted under 35 U.S.C. 154(b) by 0 days.

(21) Appl. No.: 09/424,990
(22) PCT Filed: Jun. 2, 1998
(86) PCT No.: PCT/JP98/02438
§ 371 (c)(1),
(2), (4) Date: Dec. 3, 1999
(87) PCT Pub. No.: WO98/55493
PCT Pub. Date: Oct. 12, 1998

(30) Foreign Application Priority Data

Jun. 3, 1997 (JP) ............................................. 9-159321

(51) Int. Cl.$^7$ ....................... A61K 31/70; C07H 19/167
(52) U.S. Cl. ..................... 514/45; 514/50; 536/27.8; 536/27.81; 536/28.53; 536/28.54
(58) Field of Search ................... 514/46, 47, 48, 514/49, 50; 536/27.8, 27.81, 28.53, 28.54

(56) References Cited

U.S. PATENT DOCUMENTS

| | | | |
|---|---|---|---|
| 5,200,514 A | 4/1993 | Chu | |
| 5,580,973 A | 12/1996 | Lee-Ruff et al. | |

FOREIGN PATENT DOCUMENTS

| | | |
|---|---|---|
| JP | 61-291595 | 12/1986 |
| JP | 62-14794 | 1/1987 |
| JP | 62-23723 | 1/1987 |
| JP | 62-23725 | 1/1987 |
| JP | 1-125325 | 5/1989 |
| JP | 4-252190 | 9/1992 |

OTHER PUBLICATIONS

Levene et al., J. of Biol. Chem, vol. 97, pp. 491–495 (1932).*
Levene et al., J. of Biol. Chem, vol. 109, pp. 623–630 (1935).*
Sproat et al., Nucleic Acid Research, vol. 18, No. 1, pp. 41–49 (1990).*
Cramer et al., Helvetica Chimica Acta, vol. 79, pp. 2114–2136 (1996).*
Sproat et al., Nucleic Acids Research, 18(1), pp. 41–49, 1990.
Cramer et al., Helvetica Chimica Acta, 79, pp. 2114–2136, 1996.
Lothrop et al., Journal of Cellular Physiology, 114, pp. 111–116, 1983.
Yehiely et al., Neurobiology of Disease, 3(4), pp. 339–355. 1997.
C. Lothrop, Jr. et al., *Journal of Cellular Physiology*, 114, 111–116 (1983).
H. Cramer et al., *Helvetica Chimica Acta*, 79,2114–2136 (1996).
T. Mori et al., *Journal of Reproduction and Development*, 38(4),285–292 (1992).

* cited by examiner

*Primary Examiner*—James Q. Wilson
(74) *Attorney, Agent, or Firm*—Wenderoth, Lind & Ponack, L.L.P.

(57) ABSTRACT

The present invention provides substances having an efficacy against tumors and viruses on which the conventional anti-tumor agents and anti-virus agents exhibit only insufficient effects, and having carcinostatic effect and anti-virus effect on various resistant tumors as well as a reduced side effect such that normal human cells will not be impaired.

The present invention relates to an anti-tumor or anti-viral substance represented by the formula (1)

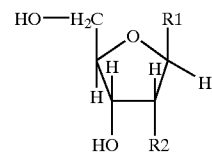

wherein R1 represents a nucleic acid base represented by a specific formula, and R2 represents a hydrogen atom, a hydroxy group or a methoxy group, or a pharmaceutically acceptable salt thereof.

The present invention also relates to a process for preparing the substance represented by the formula (1) or a pharmaceutically acceptable salt thereof, wherein NS cell which has the ability of producing the compound represented by the formula (1) is cultured, the compound represented by the formula (1) are harvested from the culture liquid, and if necessary the compound is converted into a pharmaceutically acceptable salt thereof.

Furthermore, there are also disclosed a pharmaceutical comprising the above described compound as an effective ingredient, and CD57-positive, HLA.DR-strongly positive human type natural suppressor cell.

4 Claims, 24 Drawing Sheets

NATURAL ANTITUMOR OR ANTIVIRAL SUBSTANCES AND USE OF THE SAME

TECHNICAL FIELD

The present invention relates to new compounds from natural sources which are useful in the field of pharmaceuticals and inhibit the proliferation of tumor cells or viruses and exhibit antitumor or anti-viral effects, the process for preparing the compounds, their uses, and the cells for producing the compounds.

More particularly, the present invention relates to the culture products of the cell line derived from human placenta deciduae, typically CD57-positive, HLA.DR-strongly positive human natural suppressor (NS) cells "CD57$^+$HLA-DR$^{bright}$NS cell line (TTK-1)" (referred to hereinafter as "NS cells") which have been further cloned from TTK-1 cells, the process for producing the culture products, their uses, and the NS cells.

BACKGROUND ART

In the field of chemical therapy of cancer, clinical applications of a number of metabolic products of microorganisms such as Bleomycin and Adriamycin have been tried, and these products have been practically used in clinical stages.

However, the effects of these products are not always satisfactory on a variety of tumors, and the clinical applicabilities have become complicated as the resistance phenomena of tumoral cells against these pharmaceuticals have been clinically revealed [see the abstracts of the 47th General Meeting of NIPPON GAN GAKKAI, pp. 12–15 (1988)].

On the other hand, it has been clarified that the maternal immune reaction to fetus is primarily controlled by decidua, and a large number of cellular groups belonging to large granular lymphocyte (LGL) with an NK cell marker have been accumulated at the decidual layer of mammals including human being of initial pregnancy [Mori, T. et Attachment A al., Immunomolecular mechanism in mammalian implantation. Endocrine. J., 41 (Suppl.): S17].

It has been recognized that the NS cell belonging to LGL is a cell group distinguished from immune T cell, B cell or macrophage, since it possesses a receptor to WGA lectin in mice and a sugar chain marker of CD57 in human beings.

It has been described that the NS cell also possesses a function for suppressing the division of cancer cells because of its function to potently suppressing the lymphocyte division reactions such as the division reaction of lymphocyte by mitogen MHC-non-restrictively or mixed lymphocyte reaction (Tilden et al., J. Immunol., 130, 1171).

However, a protein of the TGF-β family and a lipid-like material having a molecular weight of below 10,000 have been described as regards the causal factor managing the immunosuppressive effect on the cancer cell proliferation suppressive effect of the NS cell (Clark et al., J. Immunol., 144, 3008, and Mortari et al., J. Immunol., 144, 3037), but the exact structure or function of the NS cell remains ambiguous up to now and has been desired to be elucidated.

Conventional compounds having a chemical structure similar to the compound of the present invention and exerting anti-tumoral and/or anti-viral effects include fluorouracil (U.S. Pat. Nos. 2,802,005 and 2,885,396, doxifluridine (U.S. Pat. No. 4,071,680, Tegafur (GB Patent No. 1,168,391), Zidovudine; AZT (German Patent No. 3,608,606), Didanosine; ddI) (EP Laid-Open Publication No. 206497), and the like.

However, these anti-tumor agents and anti-virus agents of nucleic acid type not only are effective on limited kinds of tumor cells or viruses, but also act on normal human cell, so that these agents have high toxicities and become an object of public concern.

DISCLOSURE OF THE INVENTION

The present invention has been conducted in view of such problems in prior art, and the object of the present invention consists in searching for a substance in human cell metabolites having an efficacy against cancers, viruses and the like on which conventional anti-tumor agents and anti-virus agents exhibit only-insufficient effects, and providing a material which has carcinostatic effect on various resistant cancers and anti-virus effect as well as a reduced side effect such that normal human cells will not be impaired.

The present inventors have conducted earnest researches in order to accomplish the object and, as a result, have found that NS cell line induces the cell death of K562, Molt4, U937, BeWo, GCIY human cancer cells due to apoptosis, suppress the cytokinesis of cancer cells, and also found the nucleic acid type substances (referred to as AIF) which is secreted by the cell line and induces the cancer cell death due to apoptosis, and have isolated and purified the substances to determine the structures thereof. The inventors have believed that these substances can be developed and applied as a natural type carcinostatic agent and anti-virus agent as well as a pharmaceutical based on the quite new idea and having fewer side-effects.

The present inventors have cultured the NS cell having the ability for producing the compound of the formula (1) and derived from human placental decidua, collected the compound of the formula (1) from the culture fluid (supernatant and cells, especially supernatant), converted it into a pharmaceutically acceptable salt, if necessary, to obtain the compound represented by the formula (1)

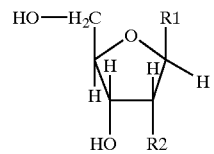

wherein
R1 represents the group

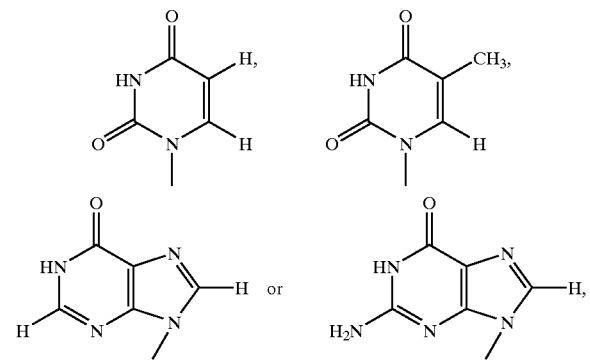

R2 represents a hydrogen atom, a hydroxy group or a methoxy group,
or a pharmaceutically acceptable salt thereof, and found that the compound of the formula (1) or a pharmaceutically acceptable salt thereof induces the human cancer cell death due to apoptosis, suppresses the proliferation of cancer cells, and exhibits anti-tumor effect or anti-virus effect. The present invention has been thus accomplished.

That is to say, the present invention relates to the anti-tumor or anti-virus substance represented by the above described formula (1), wherein R1 and R2 have the same meanings. as defined above, or a pharmaceutically acceptable salt thereof, the process for preparing the same, a pharmaceutical containing the anti-tumor or anti-virus substance represented by the above described formula (1) or a pharmaceutically acceptable salt thereof as an effective ingredient, the use of the above described compound to the preparation of a pharmaceutical and therapy, and the CD57 positive, HLA.DR strongly positive NS cell derived from human placental decidua.

BEST MODE FOR CARRYING OUT THE INVENTION

The present invention is described below in detail.

First of all, a variety of terminologies and definitions referred herein are described.

The compounds of the formula (1) are obtained by physico-chemically separating and purifying the apoptosis inducing factor (AIF) in the supernatant of the NS cell line culture, and represented by the formula (1)

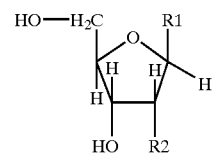

wherein

R1 represents the group

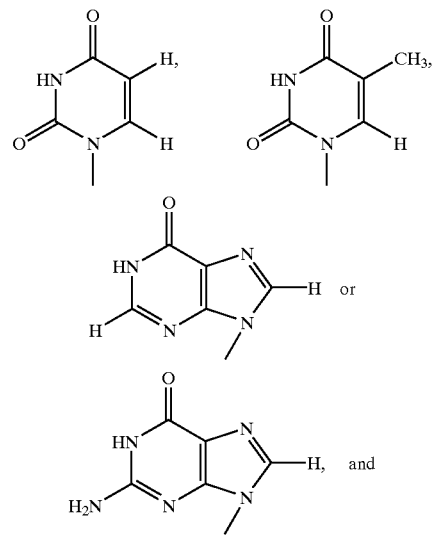

R2 represents a hydrogen atom, a hydroxy group or a methoxy group, these compounds being referred as P1, P2, P3, P4, P5 and P6, respectively in connection to the active fractions obtained by reverse phase high performance liquid chromatography.

The terminologies "P1, P2, P3, P4, P5 and P6" herein means specifically 2'-deoxyuridine, ribothymidine, 2'-O-methyluridine, thymidine, 2'-O-methylinosine, and 2'-O-methylguanosine, respectively.

That is to say, the compound represented by formula (1).

wherein R1 and R2 represent

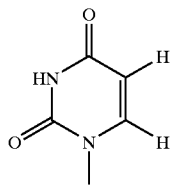

and a hydrogen atom, respectively, is P1;

wherein R1 and R2 represent

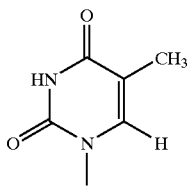

and a hydroxy group, respectively, is P2;

wherein R1 and R2 represent

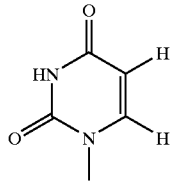

and a methoxy group, respectively, is P3;

wherein R1 and R2 represent

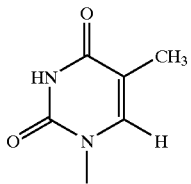

and a hydrogen atom, respectively, is P4;

wherein R1 and R2 represent

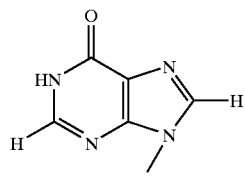

and a methoxy group, respectively, is P5; and wherein R1 and R2 represent

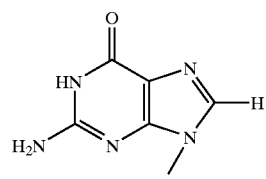

and a methoxy group, respectively, is P6.

Figure 1:
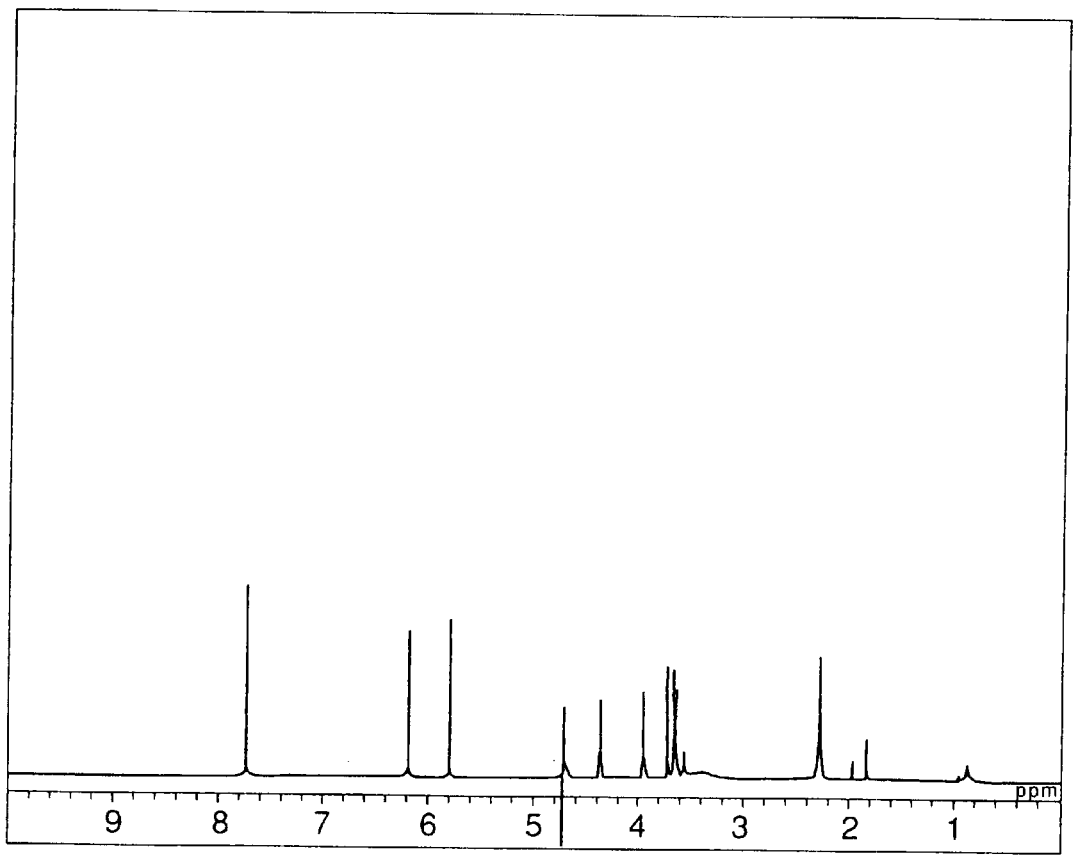
FIG. 1 represents the NMR chart of the compound P1.
Figure 2:
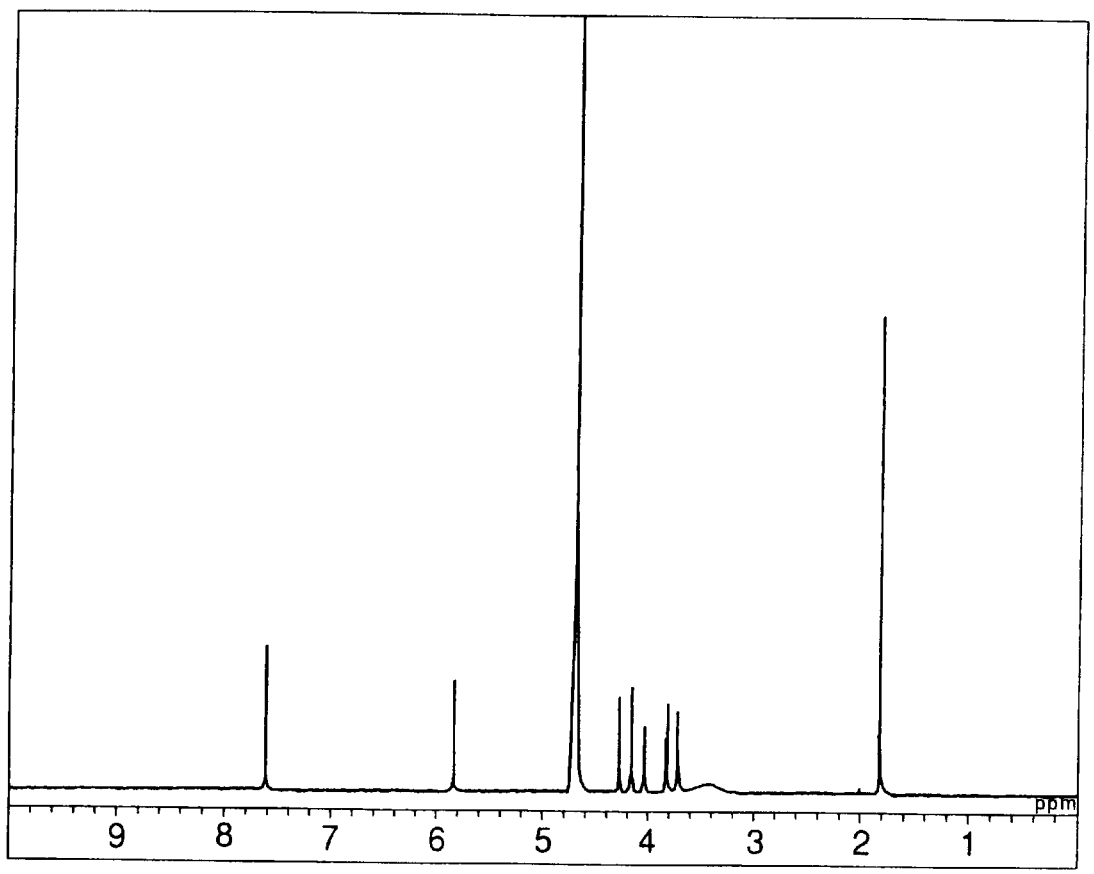
FIG. 2 represents the NMR chart of the compound P2.
Figure 3:
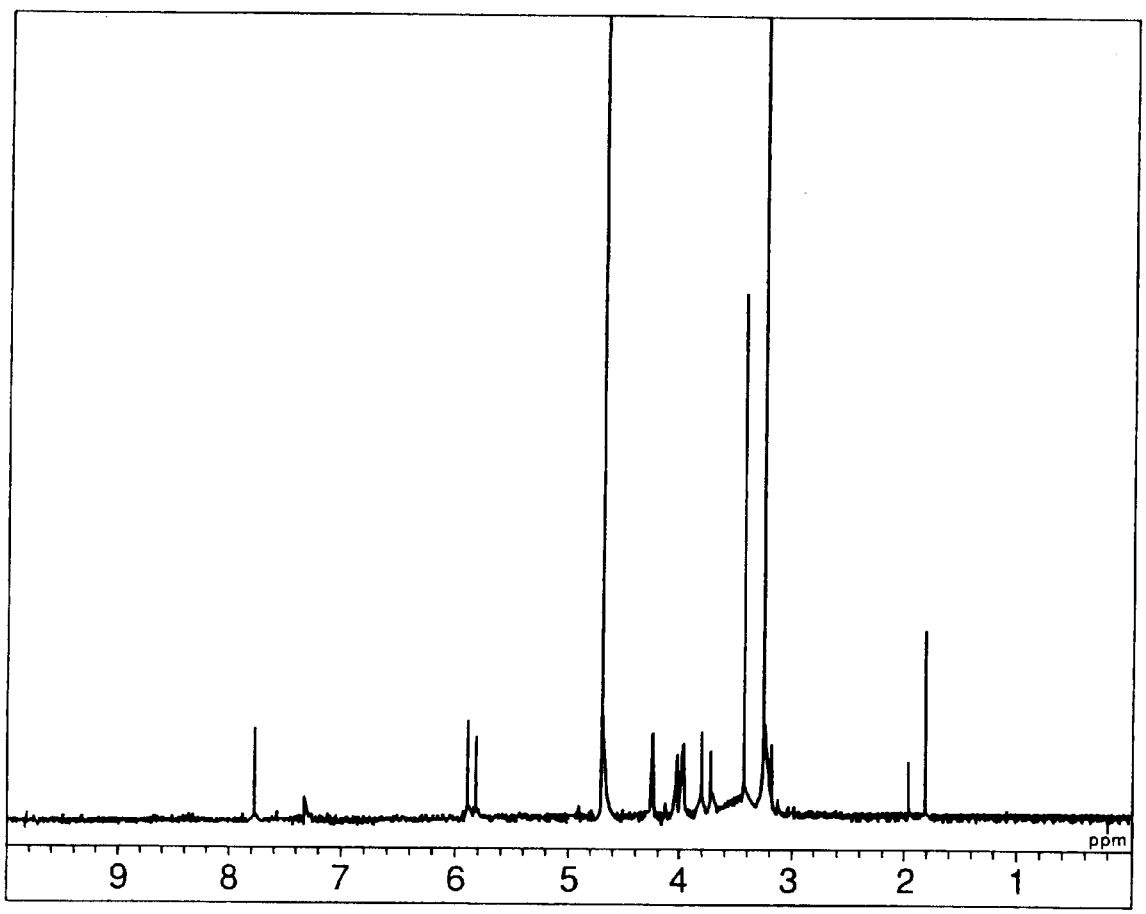
FIG. 3 represents the NMR chart of the compound P3.
Figure 4:
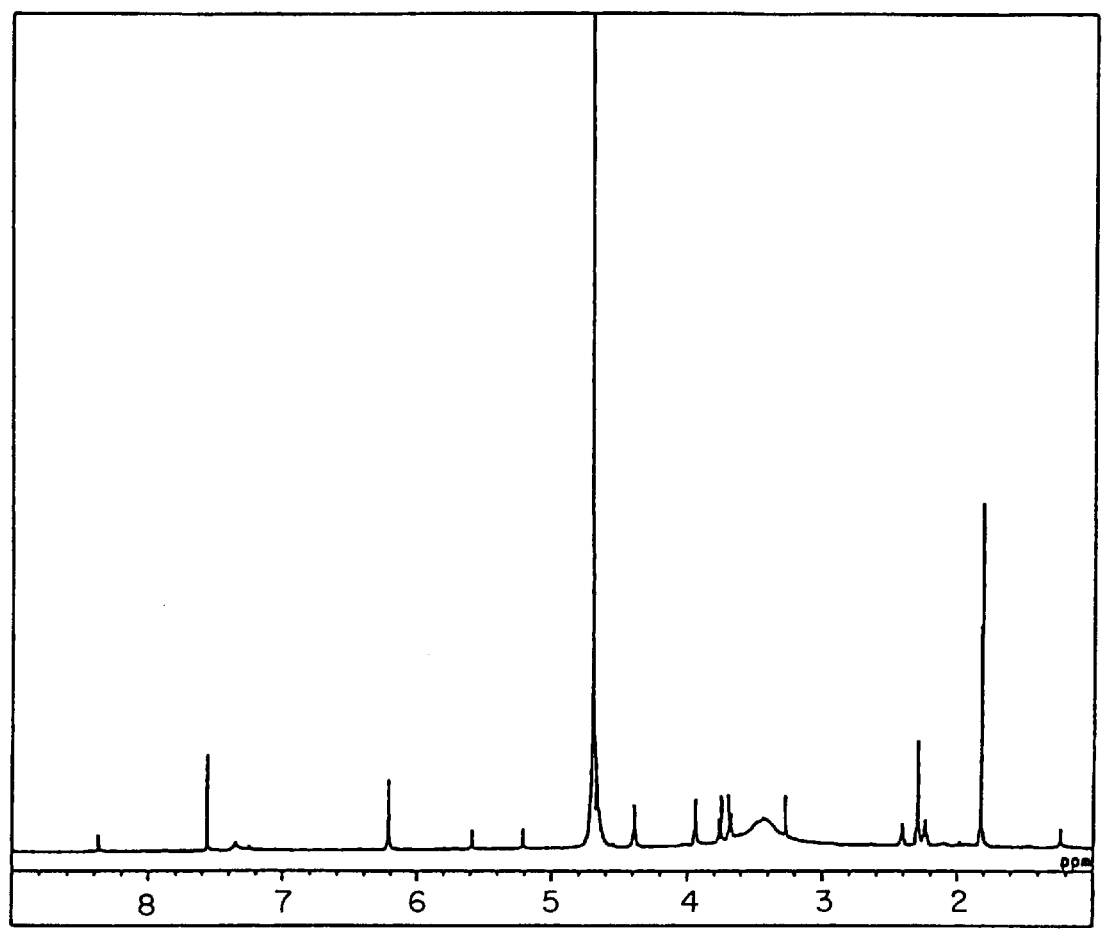
FIG. 4 represents the NMR chart of the compound P4.
Figure 5:
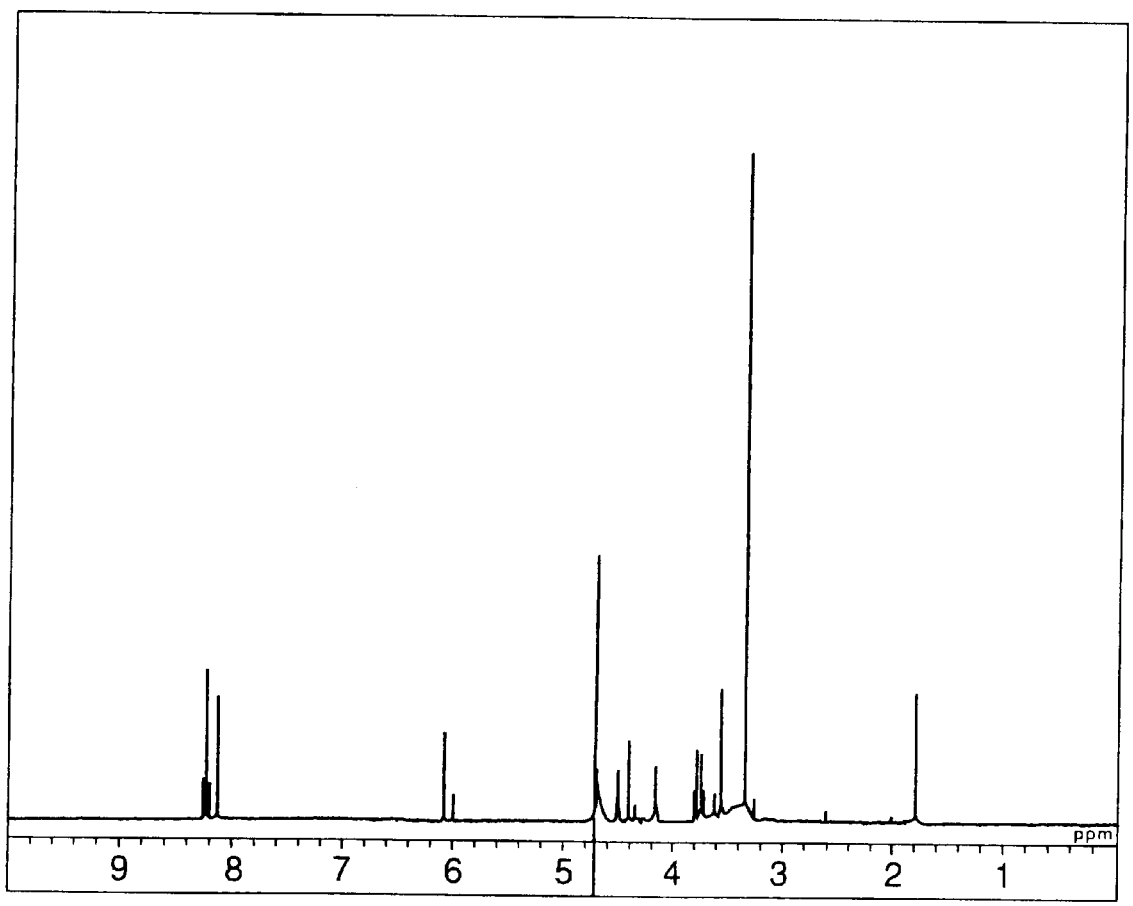
FIG. 5 represents the NMR chart of the compound P5.
Figure 6:
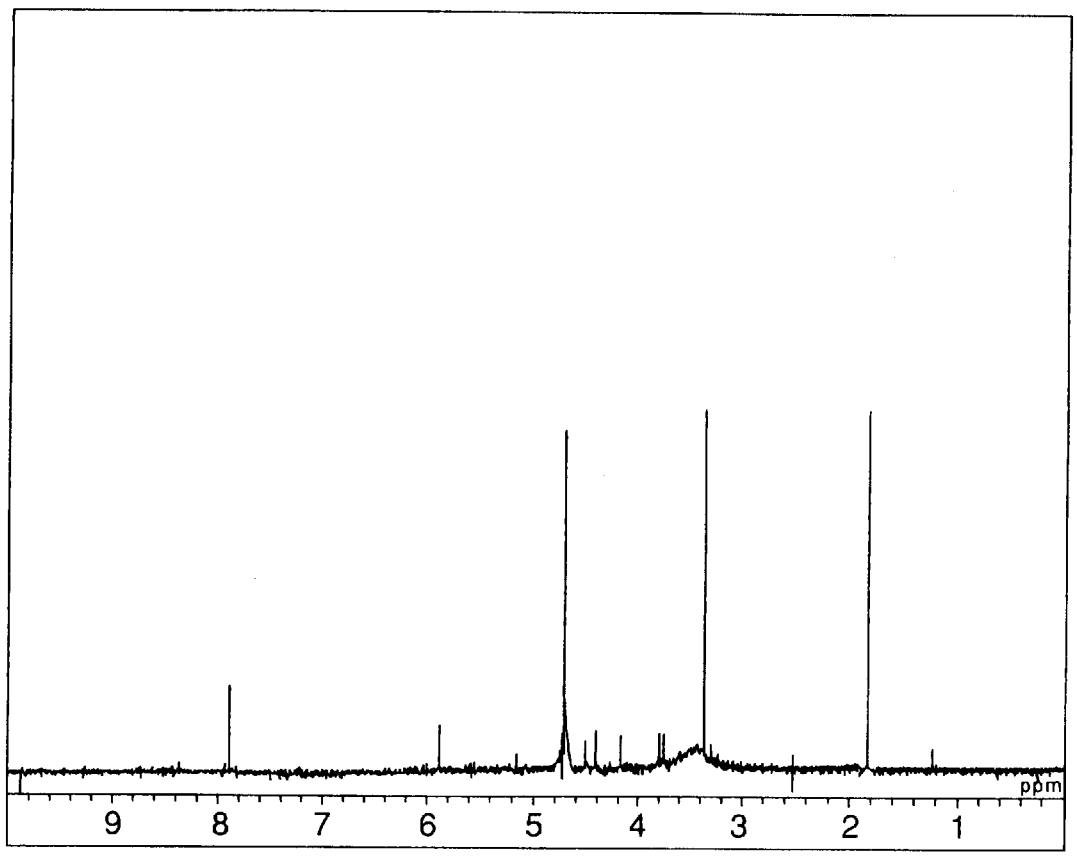
FIG. 6 represents the NMR chart of the compound P6.
Figure 7:
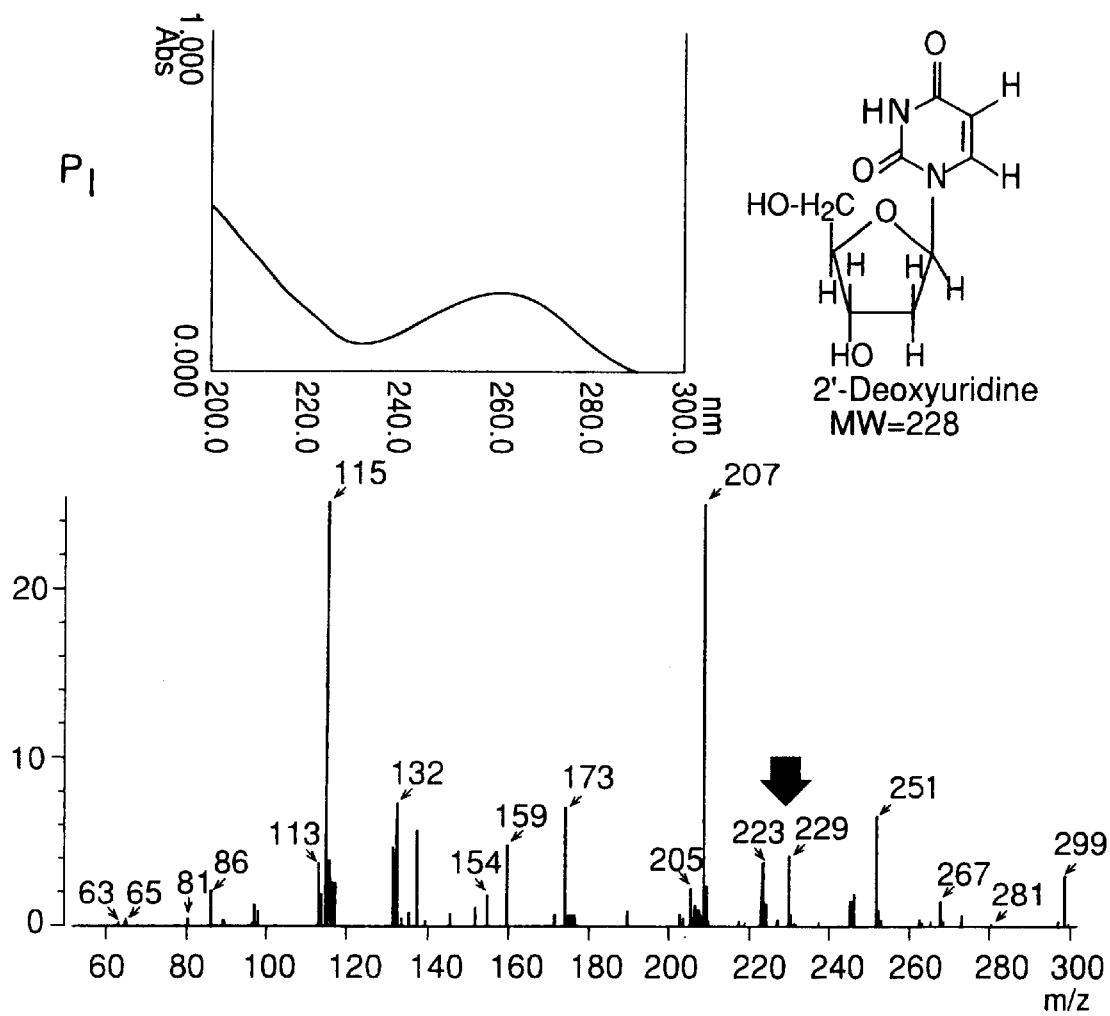
FIG. 7 represents the UV and mass spectra and the structural formula of AIF (P1)
Figure 8:
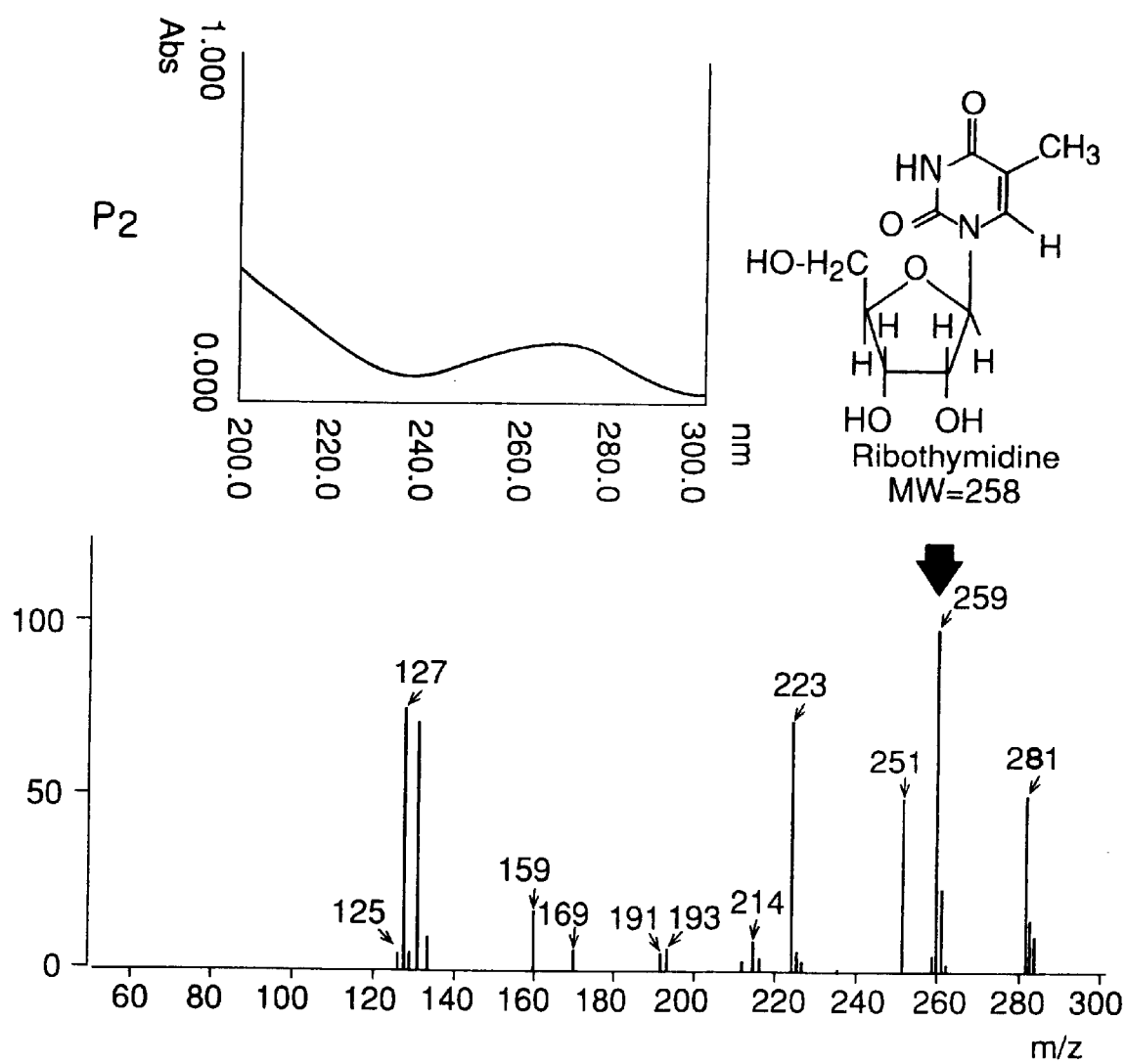
FIG. 8 represents the UV and mass spectra and the structural formula of AIF (P2)
Figure 9:
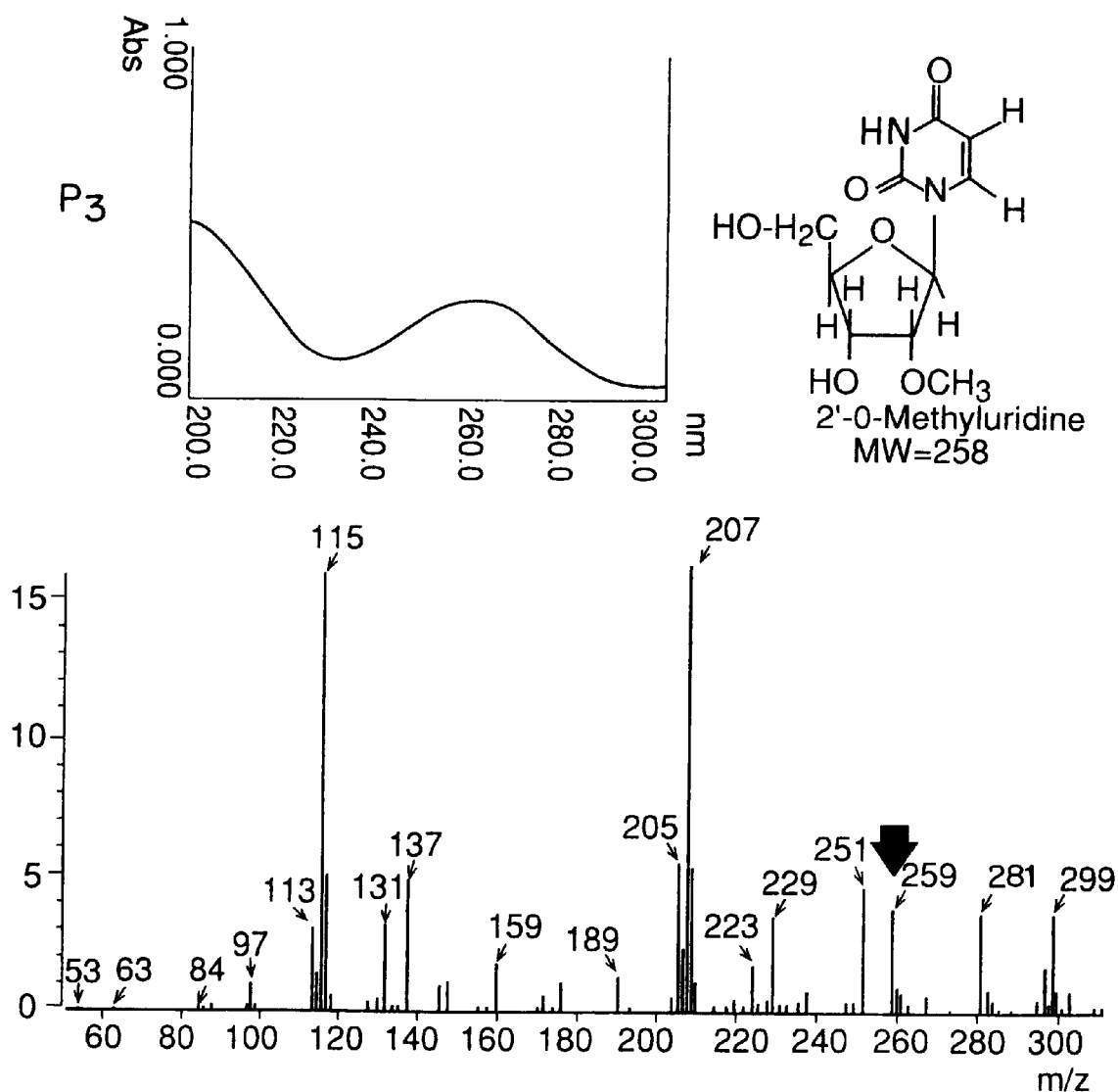
FIG. 9 represents the UV and mass spectra and the structural formula of AIF (P3)
Figure 10:
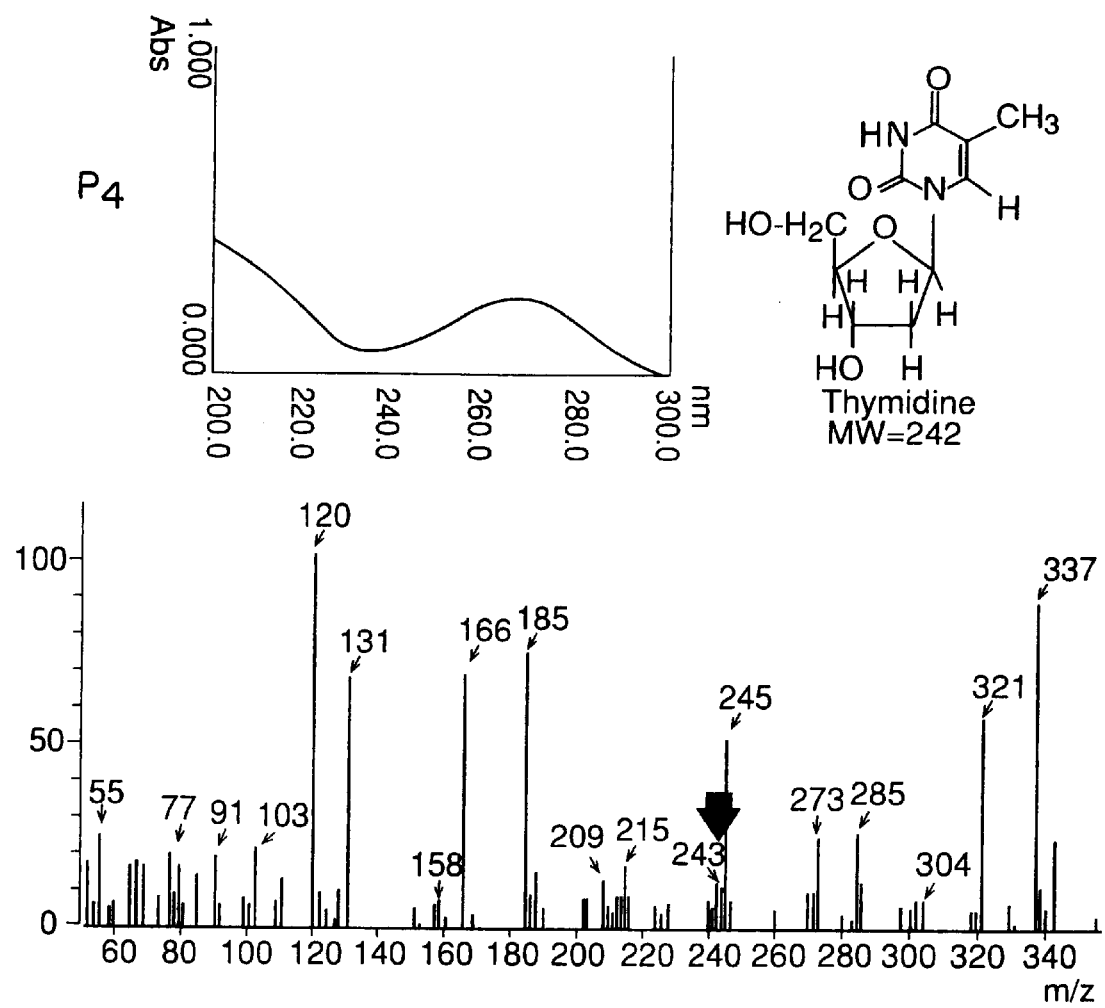
FIG. 10 represents the UV and mass spectra and the structural formula of AIF (P4)
Figure 11:
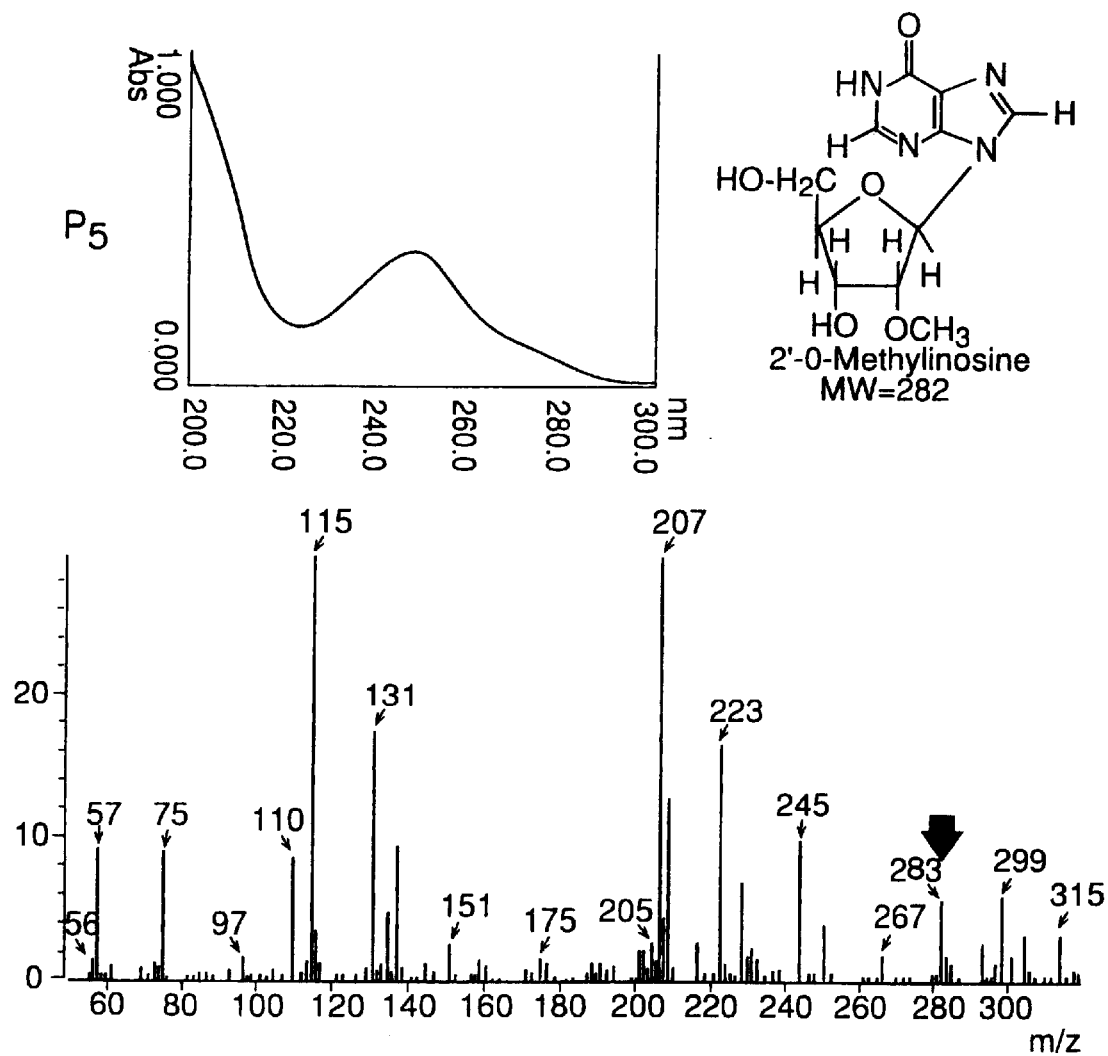
FIG. 11 represents the UV and mass spectra and the structural formula of AIF (P5)
Figure 12:
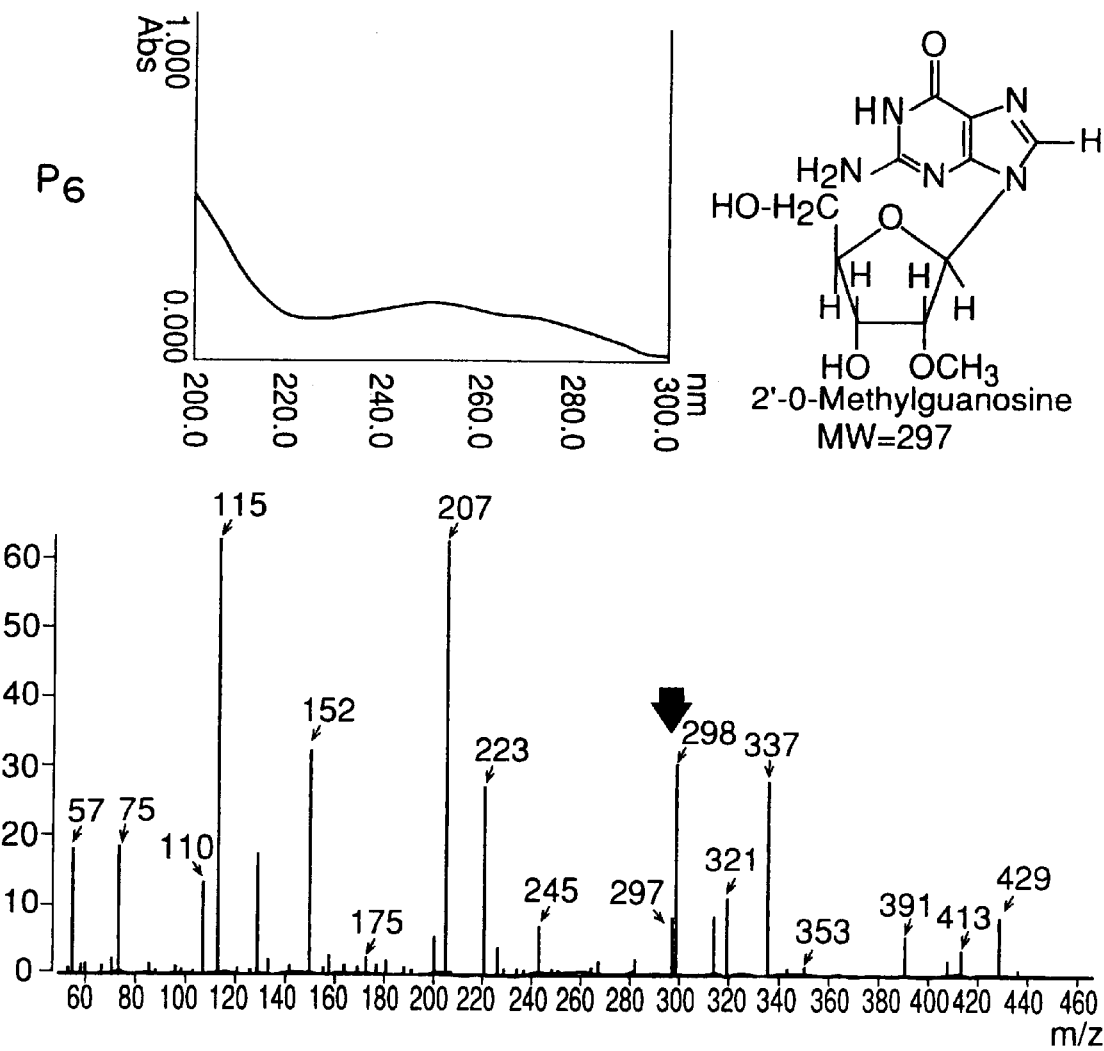
FIG. 12 represents the UV and mass spectra and the structural formula of AIF (P6)

The physico-chemical properties of the typical compounds of the present invention are listed in the followings:

a) Physico-chemical property of P1 nature: colorless crystal; molecular formula: $C_9H_{12}N_2O_5$; mp: 165°C.; mass spectrum: high-resolution FAB-MS; m/z 229 [M+1]; UV spectrum: λ[$H_2O$ (pH 7.2), max 258.5 nm]; $^1$H-NMR spectrum (300 MHz, $CDCl_3$, δ ppm): NMR chart of P1 is illustrated in FIG. 1; solubility: soluble in organic solvents such as methanol, dimethylsulfoxide and in water; discrimination of acidic, neutral and basic substances: basic substance; thin layer chromatography (Merck, Kieselgel 60F254); Rf value: 0.64 [developing solvent: chloroform/methanol/water (60:40:8)] high performance liquid chromatography: column: TSK gel ODS-80™, 4.6×150 mm (Tosoh) mobile phase: aqueous system containing 0.1% trifluoroacetic acid with a gradient of acetonitrile containing 0.1% trifluoro acetic acid at 5%/360 min; flow rate: 0.5 ml/min; detection: UV 214 nm; retention time: 20 min.

b) Physico-chemical property of P2 nature: colorless crystal; molecular formula: $C_{10}H_{14}N_2O_6$; mp: 183–185° C.; mass spectrum: high-resolution FAB-MS; m/z 259 [M+1]; UV spectrum: λ[$H_2O$ (pH 7), max 267 nm]; $^1$H-NMR spectrum (300 MHz, $CDCl_3$, δ ppm): NMR chart of P2 is illustrated in FIG. 2; solubility: soluble in organic solvents such as methanol, dimethylsulfoxide and in water; discrimination of acidic, neutral and basic substances: basic substance; thin layer chromatography (Merck, Kieselgel 60F254); Rf value: 0.66 [developing solvent: chloroform/methanol/water (60:40:8)] high performance liquid chromatography: column: TSK gel ODS-80™, 4.6×150 mm (Toso) mobile phase: aqueous system containing 0.1% trifluoroacetic acid with a gradient of acetonitrile containing 0.1% trifluoroacetic acid at 5%/360 min; flow rate: 0.5 ml/min; detection: UV 214 nm; retention time: 29 min.

c) Physico-chemical property of P3 nature: colorless crystal; molecular formula: $C_{10}H_{14}N_2O_6$; mp: 159° C.; mass spectrum: high-resolution FAB-MS; m/z 259 [M+1]; UV spectrum: λ[$H_2O$ (pH 7), max 263 nm]; $^1$H-NMR spectrum (300 MHz, $CDCl_3$, δ ppm): NMR chart of P3 is illustrated in FIG. 3; solubility: soluble in organic solvents such as methanol, dimethylsulfoxide and in water; discrimination of acidic, neutral and basic substances: basic substance; thin layer chromatography (Merck, Kieselgel 60F254); Rf value: 0.72 [developing solvent: chloroform/methanol/water (60:40:8)] high performance liquid chromatography: column: TSK gel ODS-80™, 4.6×150 mm (Toso) mobile phase: aqueous system containing 0.1% trifluoroacetic acid with a gradient of acetonitrile containing 0.1% trifluoro acetic acid at 5%/360 min; flow rate: 0.5 ml/min; detection: UV 214 nm; retention time: 40 min.

d) Physico-chemical property of P4 nature: colorless crystal; molecular formula: $C_{10}H_{14}N_2O_5$; mp: 185° C.; mass spectrum: high-resolution FAB-MS; m/z 243 [M+1]; UV spectrum: λ[$H_2O$ (pH 7), max 267 nm]; $^1$H-NMR spectrum (300 MHz, CDCl$_3$, δ ppm): NMR chart of P4 is illustrated in FIG. 4; solubility: soluble in organic solvents such as methanol, dimethylsulfoxide and in water; discrimination of acidic, neutral and basic substances: basic substance; thin layer chromatography (Merck, Kieselgel 60F254); Rf value: 0.69 [developing solvent: chloroform/methanol/water (60:40:8)] high performance liquid chromatography: column: TSK gel ODS-80™, 4.6×150 mm (Toso) mobile phase: aqueous system containing 0.1% trifluoroacetic acid with a gradient of acetonitrile containing 0.1% trifluoroacetic acid at 5%/360 min; flow rate: 0.5 ml/min; detection: UV 214 nm; retention time: 50 min.

e) Physico-chemical property of P5 nature: colorless crystal; molecular formula: $C_{11}H_{14}N_4O_5$; mp: 210–212° C.; mass spectrum: high-resolution FAB-MS; m/z 283 [M+1]; UV spectrum: λ[H$_2$O (pH 7), max 283 nm]; $^1$H-NMR spectrum (300 MHz, CDCl$_3$, δ ppm): NMR chart of P5 is illustrated in FIG. 5; solubility: soluble in organic solvents such as methanol, dimethylsulfoxide and in water; discrimination of acidic, neutral and basic substances: basic substance; thin layer chromatography (Merck, Kieselgel 60F254); Rf value: 0.67 [developing solvent: chloroform/methanol/water (60:40:8)] high performance liquid chromatography: column: TSK gel ODS-80™, 4.6×150 mm (Toso) mobile phase: aqueous system containing 0.1% trifluoroacetic acid with a gradient of acetonitrile containing 0.1% trifluoro acetic acid at 5%/360 min; flow rate: 0.5 ml/min; detection: UV 214 nm; retention time: 64 min.

f) Physico-chemical property of P6 nature: colorless crystal; molecular formula: $C_{11}H_{15}N_5O_5$; mp: 218–220° C.; mass spectrum: high-resolution FAB-MS; m/z 298 [M+1]; UV spectrum: λ[H$_2$O (pH 11, pH 1), max 258 nm at pH 11, 256 nm at pH 1]; $^3$H-NMR spectrum (300 MHz, CDCl$_3$, δ ppm): NMR chart of P6 is illustrated in FIG. 6; solubility: soluble in organic solvents such as methanol, dimethylsulfoxide and in water; discrimination of acidic, neutral and basic substances: basic substance; thin layer chromatography (Merck, Kieselgel 60F254); Rf value: 0.59 [developing solvent: chloroform/methanol/water (60:40:8)] high performance liquid chromatography: column: TSK gel ODS-80™, 4.6×150 mm (Toso) mobile phase: aqueous system containing 0.1% trifluoroacetic acid with a gradient of acetonitrile containing 0.1% trifluoroacetic acid at 5%/360 min; flow rate: 0.5 ml/min; detection: UV 214 nm; retention time: 83 min.

The cytological properties of the cell line of the present invention are listed in the followings:

1) Morphology of cell: large granular lymphocyte;
2) origin of cell: decidual tissue cell separated from placenta of human 7 week pregnant;
3) Subculture: capable of permanent proliferation;
4) Growth factor requirement: it is capable of proliferation in the medium free of normal human endometrium cell growth factor or heparin;
5) Cell maintenance, proliferation condition, proliferation dependency: the present cell line is maintained and proliferated satisfactorily under the temperature condition of generally 36–38° C., preferably at 37° C., and under the pH condition of 6.5–7, preferably 7.0;
6) Cell proliferation ability: when $2\times10^5$/ml of the present cell is cultured under the above described condition, it reaches the density of at least $5\times10^5$/ml of the cell after 3 days;
7) Function: it is not decidual interstitial cell because of no estrogen and progesterone receptors. It produces nucleic acid type functional materials, and thereby suppresses the lymphocyte division caused by MLR or mitogen irritation;
8) Form of colony: it forms colony on Petri dish, but not in soft agar;
9) Storage by freezing: it is possible to be stored at a temperature of −70° C. to −196° C. for a very long period;
10) Nature of chromosome: metacentric;
11) Confirmation by chromosome analysis: cell derived from human tissue;
12) Chromosome number: 99–100, 107–108;
13) Cell surface marker: it is immune system cell because of being CD57 positive and HLA-DR strongly positive;
14) Culture medium for maintenance and proliferation: it is satisfactorily maintained and proliferated in a 10% FCS+RPMI-1640 medium or a serum-free medium from which thymidine has been removed.

The cell strain of the present invention can be obtained for example by using the following method. That is to say, the human placental decidual cell may be obtained for example according to the method described in J. Clin. Invest., 52, 2745–2756 (1973). As a summary of the method, the cell can be obtained by sampling human endometrium or placental decidua as aseptically as possible (any tissue may be used provided it is human intrauterine tissue, and for example human placental decidual sites are preferred because of their easy availability), washing before tripsin treatment for separating the cell from connective tissue.

The cell used in the present invention may be any cell provided that it is the CD57 positive, HLA.DR strongly positive cell which is derived from human placental decidua and has an ability for producing the compound of the formula (1), but it is preferably the NS cell or its clone strain or subclone strain. The (NS) cell strain can be obtained by the derivatization into the selected cloning strain by the conventional method.

For example, it is possible to obtain a clone strain having a higher ability for producing the compound of the formula (1) by checking the amount of the compound of the formula (1) produced on the cloning of the NS cell by the conventional method. Specifically, $1\times10^5$ of TTK-1 cells were preliminarily cultured repeatedly by the limiting dilution analysis at 37° C. under the presence of 5% carbon dioxide gas so as the number of cell to be 0–1/well, and thus cellular clone having a higher ability for producing the compound of the formula (1) was selected.

In this connection, the cell line of the present invention has been deposited in National Institute of Bioscience and Human-Technology, Agency of Industrial Science and Technology,(1-3, Higashi 1-chome, Tsukuba-Shi, Ibaraki-Ken, Japan) with the acceptance number of FERM BP6350 (original deposition date: May 19, 1997)(transferred from Japanese deposition no. FERM P-16233(transfer date: May 13, 1998)).

Figure 13:
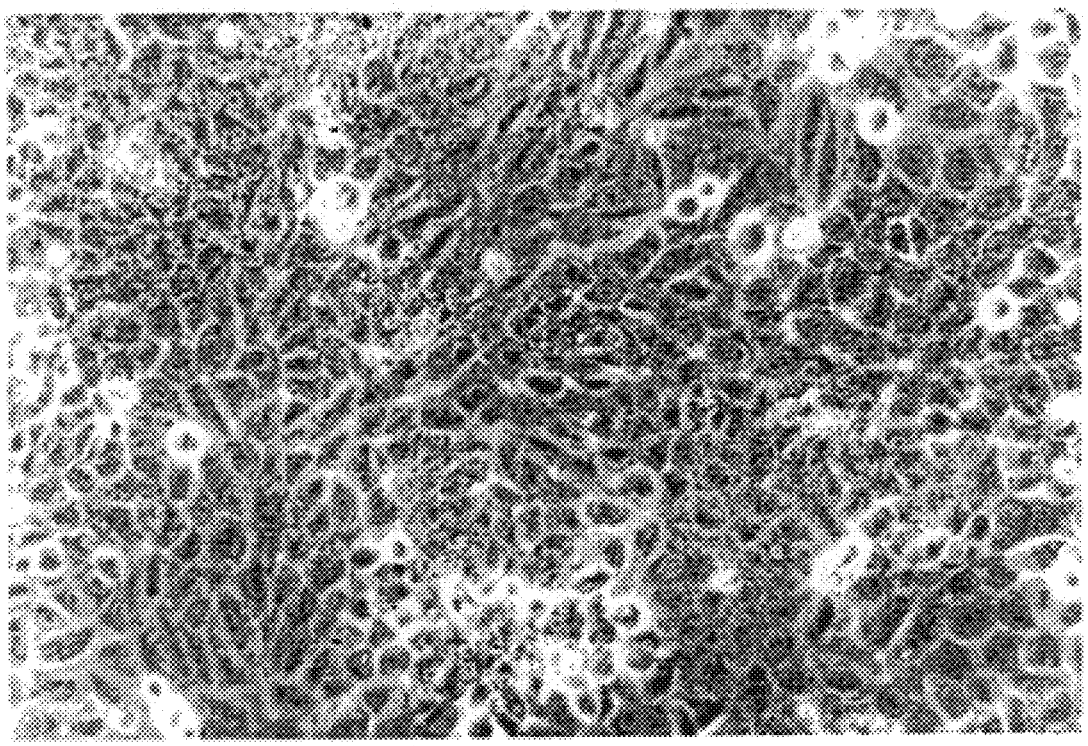
FIG. 13 is the phase-contrast micrograph of the NS cell line of the present invention, FIGS. 14 (A–G) are the photographs which show the result of the DNA fragmentation test.

Also, the phase contrast micrograph (400×) of the NS cell strain of the present invention is shown in FIG. 13. The NS cell strain adheres to culture substrate by spontaneously secreting laminin, and forms the morphology of the LGL cell strain.

The process for preparing the compounds of the present invention is described hereinafter.

The compounds of the present invention can be prepared by inoculating cells derived from human placental decidua, typically the NS cell in a nutrient containing culture medium, aerobically culturing the cells in a $CO_2$ incubator, collecting the compounds of the present invention represented by the formula (1) from the culture fluid (supernatant and cells, preferably supernatant), and optionally converting the compounds into a pharmaceutically acceptable salts.

The NS cells derived from human placental decidua thus obtained can be cultured generally in a medium used for culturing animal cells having serum added thereto, if necessary, and specifically in a usual cell culturing medium containing 20% fetal bovine serum.

As the cell culturing medium, there may be mentioned any media capable of culturing the cells such as BME medium, MEM medium (Earle. Dulbecco, High-GEM), Ham medium (F-10, F-12), ISKOF medium, 119 medium, L-15 medium, McCoy 5A medium, NCTC135 medium, Williams E medium, Waymouth medium, among which RPM1-1640 is particularly preferred.

Culture can be performed in the same manner as in the production of metabolite of general cell line, and either solid culture or liquid culture may be used. In the case of liquid culture, any culture methods including stationary culture, agitation culture, shaking culture, and aeration culture may be carried out, among which shaking culture or deep aeration-agitation culture is preferred. When the cells are cultured, the above mentioned medium preferably contains several %, particularly about 5% of carbon dioxide gas.

These media has pH values of 6–8, conveniently of about neutral value. Culture can be done at 30–40° C., preferably at about 37° C. Culturing period depends on the medium used, pH, temperature and the other conditions, but the cells can be sub-cultured usually by culturing period for 4–5 days.

In order to obtain the aimed compound of the formula (1) from the culture, there is appropriately used a separating means which is generally used for harvesting a metabolite produced by a microorganism from the culture.

The compound of the formula (1) thus produced can be purified by the known isolation-purification methods such as the solvent extraction method, the ion exchange resin method, the adsorption or partition chromatography method, and the gel filtration method singly or in combination thereof.

There can be appropriately used, for extraction and purification, an usual separation method such as reverse phase high performance liquid chromatography and thin-layer chromatography. High purification can be performed, for example, by silicagel column chromatography, ion exchange chromatography, affinity chromatography and reverse phase high performance liquid chromatography, appopriately in combination.

As is described hereinafter (in the paragraph "confirmation of the utility of the invention"), the compounds of the present invention are expected as pharmaceuticals such as a therapeutic agent of tumor and viral conditions in mammals including human.

In this connection, the compounds of the present invention may exert pharmacological effect in the phosphorylated form in vivo, and it is needless to say that such a phosphorylated compounds are also included within the scope of the invention.

Suitable tumors against which the compounds of the present invention is expected to exert the therapeutic effect include for example not only human blood cancer, but also epithelial cancers including digestive system cancers such as stomach or large intestine cancer, respiratory system cancers such as lung cancer or the like, genitalic cancers such as ovary cancer or choriocarcinoma.

Suitable viruses against which the compounds of the present invention is expected to exert the therapeutic effect include for example human retrovirus types such as HTLV, HIV, and the like.

The compounds of the formula (1) of the present invention can be also used as a pharmaceutically acceptable salts thereof, if it is used as an anti-tumor agent or an anti-virus agent.

The non-toxic salts of the present compounds represented by the formula (1) include for example the salts with inorganic acids such as hydrochloric acid, nitric acid, sulfuric acid or phosphoric acid, the salts with organic acids such as acetic acid, citric acid or tartaric acid, the salts with organic sulfonic acids such as methanesulfonic acid or p-toluenesulfonic acid, or the salts with amino acids such as aspartic acid, glutamic acid or lysine.

The pharmaceutically acceptable salts of the compounds of the present invention can be prepared by appropriately combining the conventional methods used in the art of organic synthetic chemistry. Specifically, there may be mentioned the method by neutlization titration of the solution of the free-type compound of the present invention with an acidic solution.

A variety of forms can be selected as the dosage forms when the compounds of the present invention are used as an anti-tumor agent or an anti-virus agent, and include for example oral agents such as tablet, capsule, powder, granule and liquid, and sterile parenteral liquid agents such as solution or suspension. The preparation of the present invention comprises one or more of the compounds of the present invention as the effective ingredient, and if necessary, may comprise various conventional additives such as carrier, diluent or excipient (pharmaceutical composition).

The solid preparations can be directly prepared in the forms of tablet, capsule, granule or powder, but can also be prepared with use of appropriate additives.

The additives include for example sugars such as lactose and glucose, starches such as maize, wheat and rice, fatty acids such as stearic acid, inorganic salts such as sodium metasilicate, magnesium aluminate and anhydrous calcium phosphate, synthetic polymers such as polyvinyl pyrrolidone and polyalkylene glycol, fatty acid salts such as calcium stearate and magnesium stearate, alcohols such as stearyl alcohol and benzyl alcohol, synthetic cellulose derivatives such as methyl cellulose, carboxymethyl cellulose, ethyl cellulose and hydroxypropylmethyl cellulose as well as the conventional additives such as water, gelatin, talc, vegetable oils, gum arabic, and the like.

Such solid preparations such as tablet, capsule, granule or powder may generally contain the effective ingredient in an amount of 0.1–100% by weight, preferably 5–100% by weight.

The liquid preparations can be prepared in the form of suspension, syrup, injection or the like with use of water, alcohols or the conventional additives appropriate for liquid preparations, for example, oils derived from vegetable oils such as soy bean oil, peanut oil or sesame oil.

Particularly, solvents suitable for the parenteral dosages in the form of intramuscular injection, intravenous injection, subcutaneous injection or intratumoral injection include for example distilled water for injection, aqueous lidocaine hydrochloride solution (for intramuscular injection), physiological saline, aqueous glucose solution, ethanol, liquids for intravenous injection such as aqueous solutions of citric acid or sodium citrate, electrolyte solutions such as those for intravenous drop or intravenous injection, or admixed solutions thereof.

These injections can also be prepared into powder or the one having appropriate additives added thereto which will be formed into solution on use as well as the previously dissolved forms. These injections may contain generally 0.1–10% by weight, preferably 1–5% by weight of the effective ingredient.

The oral liquid preparations such as suspension or syrup may contain 0.5–10% by weight of the effective ingredient.

The preparation of the present invention may comprise one or more of the compounds of the present invention as the effective ingredients, and the examples of the effective ingredients are preferably the one of the typical compounds of the present invention P1–P6, more preferably the combinations of two to six of these compounds.

The practically preferred dose of the compound of the present invention can be appropriately varied depending on the kinds of the compounds used, the kinds of incorporated composition, frequencies of dosage, disorder sites to be treated, and the severities of patients.

For instance, the dose per adult is in the range of 10–500 mg/day in the case of oral administration, and 10–100 mg/day in the case of parenteral administration, preferably intravenous injection. In this connection, frequencies of dosage vary depending on the dosage manners and conditions, but the compound can be administered at one time in a single dose or in portions in two to five doses.

CONFIRMATION OF THE UTILITY OF THE INVENTION

Summary

The CD57-positive HLA.DR-strongly positive natural suppressor (NS) cell strain derived from human placental decidual tissue induces the apoptosis of human cancer cells such as K562, Molt4, U937, GCIY, and BeWo, and suppresses the proliferation of these cells. The apoptosis inducing factor (AIF) is produced and released in the supernatant of the NS cell line culture. Thus, the AIF produced by the NS cell was separated and purified by the physico-chemical methods. The activity of AIF was measured by the ability of $^3$H-thymidine into the cell and the DNA fragmentation method. First, the supernatant of the culture of the NS cell line was adsorbed on a C18 column and eluted to separate the AIF. The crude extract was developed on a thin layer chromatography (TLC) plate, and the active fractions were isolated and purified by reverse phase high performance liquid chromatography (HPLC).

The components (P1–P6) derived from the peaks obtained by HPLC induced the cell death and suppressed the proliferation of K562, Molt4, U937, GCIY and BeWo cancer cells, but did not impaired the normal WI-38 cell derived from fetal human lung. The physical and chemical properties of these six AIFs suggested that these six AIFs are nucleic acids or their derivatives. In fact, the structural analysis of these compounds by FAB-MS and NMR indicated that P1 is 2'-deoxyuridine, P2 ribothymidine, P3 2'-O-methyluridine, P4 thymidine, P5 2'-O-methylinosine, and P6 2'-O-methylguanosine. Also, significant tumor degenerative effect was observed in an animal experiment with mice having the human cancer tissue transplanted thereinto to which these six AIFs have been administered.

Confirmation Test

AIFs finally separated and produced by HPLC were added to the target cancer cells to examine the in vitro ability of inducing apoptosis (in vitro experiment) and the therapeutic effects of AIFs on SCID mice having cancer cell inoculated thereinto (animal experiment).

[I] In Vitro Experiment

Next, in order to illustrate the usefulness of the present invention, the interaction between the NS cell line as the typical example according to the present invention and the typical one of various human-derived cancer cells as the target cell was measured directly or indirectly by the co-culture of them. The cells used were shown below:

(1) NS cell line (TTK-1) (cell line derived from human placental decidua)

It is the cell formed as a strain by culturing human placental decidual tissue cell of 7-week pregnant, and is CD57-positive HLA-DR-strongly positive natural immunosuppressive cell derived from marrow-lymphatic tissue;

(2) Molt4 (human T cell leukemia cell line);

(3) K562 (human erythroblastic leukemia cell line);

(4) U937 (human histiocytic leukemia cell line);

(5) GCIY (human stomach carcinoma cell line);

(6) BeWo (human choriocarcinoma cell line);

(7) WI-38 (normal fibroblast cell line derived from fetal human lung tissue).

The cells listed above were the ones obtained by subculture in a 10% FCS+RPMI-1640 medium or a serum-free medium from which thymidine has been removed in an incubator at 37° C. under 5% $CO_2$.

Experimental Example 1

Direct Co-culture Test of the NS Cell Line and the Molt4/K562/U937/GCIY/BeWo/WI-38 Target Cells (Direct Reaction)

Direct Co-culture Test:

NS, Molt4 (human T cell leukemia cell line), K562 (human erythroblastic leukemia cell line), U937 (human histiocytic leukemia cell line), GCIY (human stomach carcinoma cell line), BeWo (human choriocarcinoma cell line), WI-38 (normal cell line derived from fetal human lung tissue) were used, and NS ($10^4$, $10^5$, $10^6$) and Molt4/K562/U937/GCIY/BeWo/WI-38($10^6$) cells were co-cultured in 2 ml of culture medium in a 24 well plate for 24 hours–48 hours.

As a result of the direct interaction (co-culture) between the NS cell line and the target cells, DNA of the cell was extracted after 24 hours and subjected to electrophoresis on 2% agarose gel.

Figure 14A:
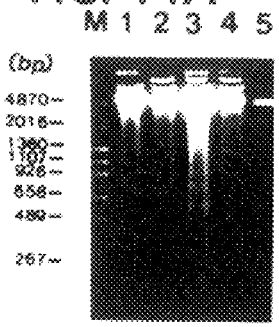

As a result, as shown in FIG. 14A, lanes 1, 2 and 3 show the results of the co-cultures with $10^4$, $10^5$ and $10^6$/well of the NS cell, respectively, and $10^6$/well of Molt4, and the degree of the DNA fragmentation in the target cell was increased depending on the numbers of the NS cell inoculated.

On the other hand, lane 4 is the result of the culture with $10^6$/well of the NS cell solely, and lane 5 is the result of the culture with $10^6$/well of Molt4 solely. In these cases, no DNA fragmentation was observed. Lane M is a marker which shows the sizes of DNAs.

Figure 14B:
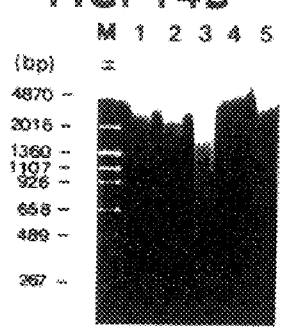

As shown in FIG. 14B, lanes 1, 2 and 3 show the results of the co-cultures with $10^4$, $10^5$ and $10^6$/well of the NS cell, respectively, and $10^6$/well of K562, and the degree of the DNA fragmentation in the target cell was increased depending on the numbers of the NS cell inoculated.

On the other hand, lane 4 is the result of the culture with $10^6$/well of K562 solely, and lane 5 is the result of the culture with $10^6$/well of the NS cell solely. In these cases, no DNA fragmentation was observed.

Figure 14C:
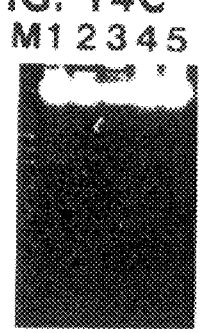

As shown in FIG. 14C, lanes 1, 2 and 3 show the results of the co-cultures with $10^6$, $10^5$ and $10^4$/well of the K562 cell and the Molt4, respectively, lane 4 shows the result of culture with $10^6$/well of Molt4 solely, and lane 5 with $10^6$/well of K562 solely. In neither cases, DNA fragmentation was induced.

Figure 14D:
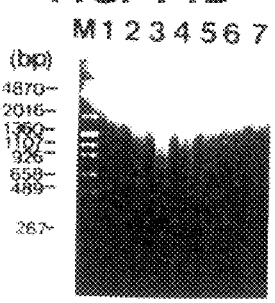

As shown in FIG. 14D, lanes 1, 2 and 3 show the results of the co-cultures with $10^4$, $10^5$ and $10^6$/well of the NS cell, respectively, and $10^6$/well of BeWo, and the degree of the DNA fragmentation in the target cell was increased depending on the numbers of the NS cell inoculated. On the other hand, lane 4 is the result of culture with $10^6$/well of NS solely, lane 5 is the result of culture with $10^6$/well of BeWo solely, lane 6 is the result of co-culture with $10^6$/well of BeWo and $10^6$/well of GCIY, and lane 7 is the result with $10^6$/well of GCIY solely. In neither cases, DNA fragmentation was observed.

Figure 14E:
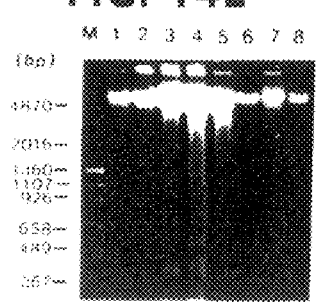

As shown in FIG. 14E, lanes 1, 2, 3 and 4 show the results of the co-cultures with $10^3$, $10^4$, $10^5$ and $10^6$/well of the NS cell, respectively, and $10^6$/well of U937, and the degree of the DNA fragmentation in the target cell was increased depending on the numbers of the NS cell inoculated.

On the other hand, lane 7 is the result of co-culture with $10^6$/well of Molt4 and $10^6$/well of U937, lane 8 is the result of culture with $10^6$/well of Molt4 solely, lane 6 with $10^6$/well of U937 solely, and lane 5 with $10^6$/well of NS. In neither cases, DNA fragmentation was induced.

Figure 14F:
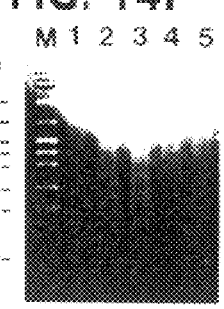

As shown in FIG. 14F, lanes 1, 2 and 3 show the results of the co-cultures with $10^4$, $10^5$ and $10^6$/well of the NS cell, respectively, and $10^6$/well of GCIY, and the degree of the DNA fragmentation in the target cell was increased depending on the numbers of the NS cell inoculated. On the other hand, lane 4 is the result of culture with $10^6$/well of GCIY solely, and lane 5 is the result of culture with $10^6$/well of NS solely. In neither cases, DNA fragmentation was observed.

Figure 14G:

As shown in FIG. 14G, lanes 1, 2 and 3 show the results of the co-cultures with $10^4$, $10^5$ and $10^6$/well of the NS cell, respectively, and $10^6$/well of WI-38, and no DNA fragmentation in the target cell was observed notwithstanding the increased numbers of the NS cell. Lane 4 is the result of culture with $10^6$/well of WI-38 solely, and lane 4 is the result of culture with $10^6$/well of NS solely. In neither cases, DNA fragmentation was induced.

That is to say, the interaction (co-culture) between the NS cell and the Molt4, K562, BeWo, U937 and GCIY cells resulted in the DNA fragmentation of the target cell after 24 hours, and the degree of the DNA fragmentation depends on the increased numbers of the NS cells.

On the other hand, the DNA fragmentation was induced in neither cases of the co-culture between the K562 and the Molt4 cells, the Molt4 and U937 cells, nor the BeWo and GCIY cells. Also, no DNA fragmentation was observed in the co-culture between the NS cell and the normal WI-38 cell. This indicates that the NS cell line does not impair normal human cell. In fact, it can be said that the NS cell line brought about the cell death of human cancer cells due to the specific apoptosis (DNA fragmentation).

Experimental Example 2

Indirect Interaction (Indirect Co-culture) in which the NS Cell and the Target K562/Molt4 Cells are Placed in a Chamber Indirect Co-culture Test:

A culture chamber for the reaction between cells having a bottom in the form of filter (diameter 0.45 μm) was inserted into a well, and Molt4/K562 cells ($10^4$) were added.

After culturing at 37° C. under 5% $CO_2$ for 3 days, the target cells were harvested and subjected to the radioisotopic $^3H$-thymidine incorporation method, the trypan blue incorporating staining method, and the DNA fragmentation method to determine the interaction between cells.

Figure 15:
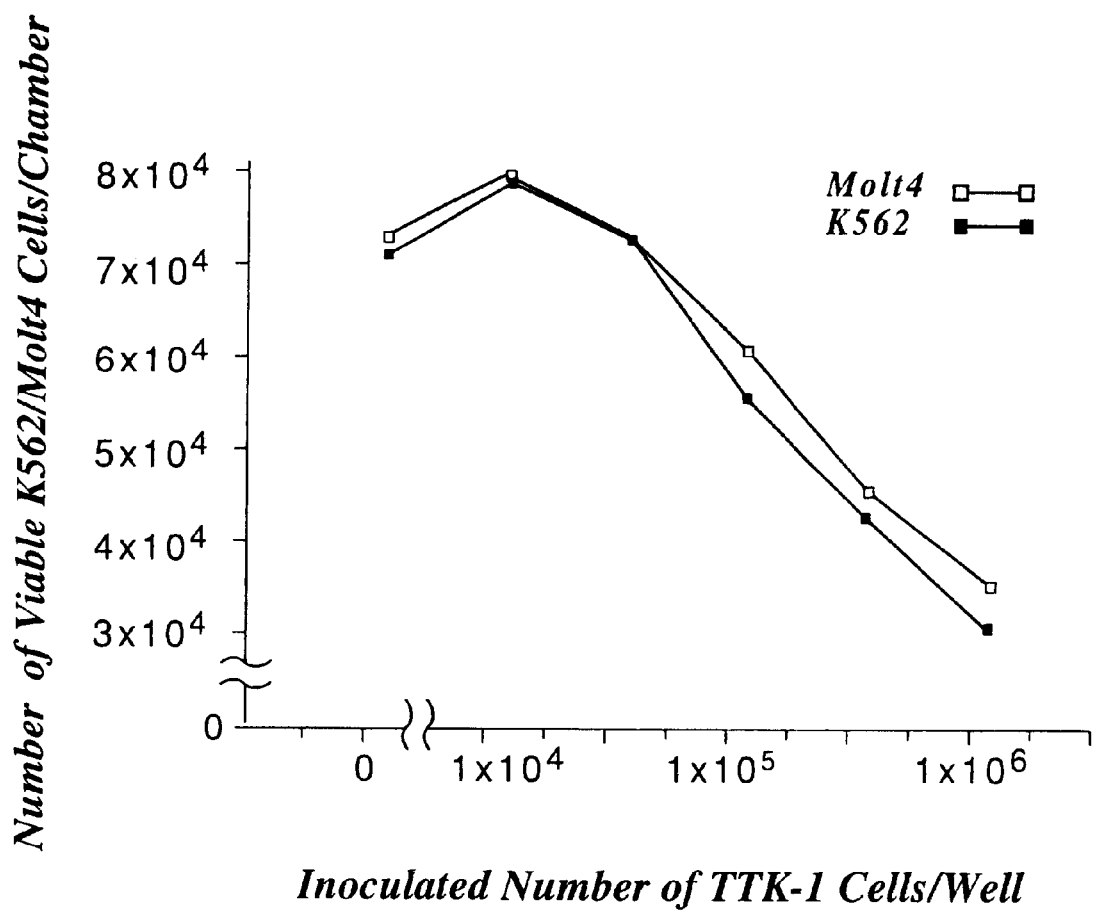
FIG. 15 represents the graph which show the result of the indirect coculture of the NS cells and the target cell, FIGS. 16 (A, B) represent the graphs which show the suppression of incorporation of $^3$H-thymidine into the target cells by AIF from NS (TTK-1) cell supernatant (sup), FIGS. 17 (A, B) are the photographs which show the result of the DNA fragmentation test of the target cells by AIF, FIGS. 18 (A–C) are the HPLC charts of AIF, FIG. 19 represent the graphs which show the suppression of incorporation of $^3$H-thymidine, FIGS. 20 (A–C) are the photographs which show the result of the DNA fragmentation test of the target cells by AIF, FIGS. 21 (A–D) are the photographs which show the result of the DNA fragmentation test of the target cells by AIF.

In this system, the number of the target cancer cells within the chamber was decreased along with the increase of the number of the NS cell after 72 hours (FIG. 15).

This experimental result indicates that the NS cell produces a low-molecular weight soluble material which passes through the Millipore membrane in the chamber and brings about the target cancer cell death.

Experimental Example 3

Confirmation Test of the Suppression of Incorporation of $^3H$-thymidine into the Target Cell and the DNA Fragmentation by Crude-extracted AIF by Thin Layer Chromatography (TLC)

The sample lyophilized from 50 ml of the supernatant of the NS cell line culture was subjected to chromatography on a C18 column (BONDELUTE), and the fraction retained in the column was separated and eluted with acetonitrile and methanol, and concentrated to dryness by evaporating the solvents with nitrogen gas. The fraction retained in the column suppressed the proliferation of the K562/Molt4 cells, and induced DNA fragmentation.

The fraction was further developed by TLC. That is to say, the solution of the materials separated on the C18 column in chloroform: methanol (1:1) was spotted on a thin layer and developed by chloroform: methanol: distilled water (60:40:8). After development, the plate was divided into two fractions of lower than the band (Rf=0.5) of the phenol red reagent contained in the medium (Rf<0.5, TLC-A) and upper than the band (Rf>0.5, TLC-B), and the gel on each of the fractions was scratched off and extracted with chloroform/methanol to dry the extract with nitrogen gas. There was recognized the existence of the material which suppresses the proliferation of the K562/Molt4 cells (FIG. 16A-B) and induces DNA fragmentation (FIG. 17A-B) in the fraction (U) upper than the position of phenol red (Rf 0.5) in TLC.

As a control, in the fresh medium used or in the supernatant of the culture of the target K562/Molt4 cells, no production of a material which suppresses the proliferation of the target cells or induces DNA fragmentation was recognized. It was thus confirmed that a material (AIF) which can induce the apoptosis (cell death) of human cancer cell is produced in the supernatant of the NS cell line culture, and that AIF is found in the fraction which moves more rapidly than phenol red on TLC (Rf of phenol red=0.5).

Experimental Example 4

Test for Suppressing the Incorporation of $^3H$-thymidine into the Target Molt 4 Cell by AIF Finally Separated and Purified by HPLC The active fraction B on TLC was separated and purified on an ODS-80™ column (Tosoh) by elution with acetonitrile containing 0.1% trifluoroacetic acid with a gradient of 0–5%/360 min at a flow rate of 0.5 ml/min while monitoring OD at 214 nm.

All of the samples obtained from six main peaks (1–6) (FIG. 18A, HPLC chart) suppressed the incorporation of $^3H$-thymidine into the Molt4 cell. Particularly, the samples from the peaks 1 and 4 showed strong activity, and a mixed sample of 1/10 dilutions of these peaks (0.7 μg/ml) also showed strong activity (FIG. 19).

As shown in column M, it shows the synergistic effect of these peaks (AIF).

Experimental Example 5

Critical Amount of AIF which is Capable of Inducing the DNA Fragmentation of the Molt4 Cell.

As shown in FIGS. 20A and 20B, the samples derived from the respective active peaks (1–6) separated by HPLC (A: 7 $\mu$g/ml, B: 7×3$^{-2}$ $\mu$g/ml) were reacted with 5×10$^5$ of the Molt4 cell, and DNA of the target cell was extracted and subjected to electrophoresis on 2% agarose gel. At the concentrations of 7 $\mu$g/ml and 7×3$^{-2}$ $\mu$g/ml, the DNA fragmentation of the Molt4 cell was recognized, but the effect disappeared at a low concentration of 7×3$^{-5}$ $\mu$g/ml as shown in FIG. 20C.

Experimental Example 6

DNA Fragmentation Test of the Target BeWo Cell with AIF Finally Separated by HPLC As shown in FIG. 21A, the samples derived from the respective peaks (1–6) separated by HPLC (21 $\mu$g/ml) were reacted with the BeWo cell for 48 hours, and DNA of the BeWo cell was extracted and subjected to electrophoresis on 2% agarose gel. All of the peaks induced the DNA fragmentation of the BeWo cell (FIG. 21A).

Experimental Example 7

DNA Fragmentation Test of the Target U937 Cell with AIF Finally Separated by HPLC As shown in FIG. 21B, the samples derived from the respective peaks (1–6) separated by HPLC (21 $\mu$g/ml) were reacted with the U937 cell for 48 hours, and then DNA of the U937 cell was extracted and subjected to electrophoresis on 2% agarose gel. All of the peaks induced the DNA fragmentation of the U937 cell (FIG. 21B).

Experimental Example 8

DNA Fragmentation Test of the Target GCIY Cell with AIF Finally Separated by HPLC As shown in FIG. 21C, the samples derived from the respective peaks (1–6) separated by HPLC (21 $\mu$g/ml) were reacted with the GCIY cell for 48 hours, and then DNA of the GCIY cell was extracted and subjected to electrophoresis on 2% agarose gel. All of the peaks induced the DNA fragmentation of the GCIY cell (FIG. 21C).

Experimental Example 9

DNA Fragmentation Test of the Normal Human Cell WI-38 with AIF Finally Separated by HPLC As shown in FIG. 21D, the suppression of cell proliferation or DNA fragmentation were not induced with the normal human cell WI-38 as the target cell even if three-fold amounts (63 $\mu$g/ml) of the samples derived from respective peaks (1–6) were dosed. This corresponds, as shown in FIG. 14G, to the result that the direct reaction of the NS cell and the WI-38 cell causes no impairment of the normal cell.

The experimental results of this series have important meaning. That is to say, these results indicate that AIF separated and purified according to the present invention causes specifically cell death due to apoptosis (DNA fragmentation) to cancer cells, but not impair the normal cell, in other words, the normal cell can be developed as an ideal anti-cancer agent having no side effects on administeration to a cancer patient.

In addition, it is possible to develop the compound of the present invention as an immunosuppressive agent, as immunosuppressive agents in the prior art exhibit their effect by the lymphocyte division inhibitory pharmacological effect.

When the supernatant of the Molt4 cell culture or the fresh medium as the final separation control was treated in the same manner as the NS cell line culture medium and finally subjected to HPLC, such active peaks (1–6) as obtained from the NS cell line culture medium were not observed in the HPLC charts (FIGS. 18B, C).

On the other hand, the same pattern as that of the supernatant of the NS cell line culture was observed in the HPLC chart of the sample obtained by the destruction of the NS cell line itself followed by the extraction. This indicates that the NS cell itself contains the same active peaks (1–6) as those in the supernatant of the culture.

The results of the in vitro experiments described above can be summed up as follows:
(1) "The NS Cell Line Induces the Cell Death of Target Cancer Cells Due to Apoptosis"

As a result of the direct interaction (co-culture) between the NS cell and the K562, Molt4, BeWo, U937 and GCIY cells, the DNA fragmentation of the target cells were recognized after 24 hours (FIGS. 14A, B, C, D, E, F).

The degree of the DNA fragmentation in the target cell was increased depending on the numbers of the NS cell inoculated. On the other hand, DNA fragmentation was not induced in the co-cultures between K562 and Molt4 cells (FIG. 14C), Molt4 and U937 cells or GCIY and BeWo cells. In addition, DNA fragmentation was not recognized in the co-culture between the NS cell and the WI-38 cell (FIG. 14G). This result indicates that the NS cell does not impair normal human cell. In other words, it was recognized that only the NS cell has an ability to induce apoptosis specific to human cancer cells.
(2) "The NS Cell Line Releases AIF into Supernatant of Culture"

In the indirect interaction (indirect co-culture) system in which the NS cell and the target K562/Molt4 cells are placed in a chamber, the number of the target leukemia cells within the chamber was decreased along with the increase of the number of the NS cell after 72 hours (FIG. 15). In addition, the DNA fragmentation of the target leukemia cells in the chamber was also recognized. The experimental result indicates that the NS cell produces a soluble low-molecular weight material which passes through the Millipore membrane in the chamber and brings about the target leukemia cell death.
(3) "AIF Crude-purified by Thin Layer Chromatography (TLC) Suppresses the Incorporation of $^3$H-thymidine into the Target Cells and Induces the DNA Fragmentation"

The sample lyophilized from about 50 ml of the supernatant of the NS (TTK-1) cell line culture was subjected to chromatography on a C18 column, and the fraction retained in the column, which was eluted with acetonitrile and concentrated, suppressed the proliferation of the K562/Molt4 cells, and induced the DNA fragmentation.

The fraction was further applied to TLC. It was recognized that a material which suppresses the division of K562/Molt4 cells (FIGS. 16A, B) and induces the DNA fragmentation (FIGS. 17A, B) is present in the fraction upper than the position of phenol red (Rf 0.5) in TLC (Rf>0.5, TLC-B).

As a control, in the fresh serum-free medium (SFM) used or in the supernatant of the target K562/Molt4 cell culture, no production of a material which induces DNA fragmentation was recognized.

It was thus confirmed that a material (AIF) which can induce the apoptosis (cell death) of human cancer cells is produced in the supernatant of the NS cell line culture, and that AIF is found in the fraction (Rf>0.5) which moves more rapidly than phenol red on TLC (Rf of phenol red=0.5).

(4) "AIF Finally Separated and Purified by HPLC Induces the DNA Fragmentation of Target Cells"

The total active fraction (TLC-B) crude-purified from 500 ml of the supernatant of the NS cell culture by TLC was separated and purified by reverse-phase HPLC on an TSK gel ODS-80™ column (Tosoh).

Six main peaks (1–6) were obtained (FIG. 18A, HPLC chart).

All of the samples from respective peaks 1–6 (7 μg/ml) suppressed the incorporation of $^3$H-thymidine into the Molt4 cell, in other words, these samples suppressed the division of the Molt4 cell. Particularly, the samples from the peaks 1 and 4 showed strong activity, and a mixed sample of 1/10 dilutions of the peaks (0.7 μg/ml, respectively) also showed strong activity (FIG. 19). As shown in column M of FIG. 19, it indicates the synergistic effect of these peaks (AIF).

(5) "Critical Amount of AIF which is Capable of Inducing the DNA Fragmentation of the Molt4 Cell"

Corresponding to the Molt4 cell division suppressive effect of the active peaks (1–6), the samples derived from the respective peaks (1–6) (7 μg/ml) induced the DNA fragmentation of the Molt4 cell (FIG. 20A).

When the Molt4 cell was treated with each sample ($7 \times 3^{-2}$ μg/ml) derived from the active peaks separated by HPLC for 48 hours, the DNA fragmentation of the target cell was recognized (FIG. 20B), but the effect disappeared at a low concentration of $7 \times 3^{-5}$ μg/ml (FIG. 20C).

(6) When BeWo, U937 and/or GCIY were used as the target cell, the samples derived from the peaks (1–6) (21 μg/ml) and the 1/10 fold diluted mixed samples (2.1 μg/ml, respectively) induced the DNA fragmentation (FIGS. 21A, B, C).

Also, when human normal cell WI-38 was used as a target, neither the suppression of cell division nor the DNA fragmentation were caused even if the samples derived from respective peaks (1–6) were added to the target in an amount of 3 times of that added to the target cancer cells (FIG. 21D). This corresponds to the result that the normal cell is not impaired in the direct interaction of the NS cell and the WI-38 cell. This experimental result has an important meaning. That is to say, the result indicates that AIF separated and purified according to the present invention causes specifically cell death due to apoptosis (DNA fragmentation) to cancer cells, but hardly impair the normal cell, in other words, the normal cell can be developed as an ideal anticancer agent having no side effects on administeration to a cancer patient. Furthermore, when the supernatant of the Molt4 cell culture or the fresh medium was treated in the same manner as the NS cell line culture medium and finally subjected to HPLC, such active peaks (1–6) as obtained from the TTK-1 culture medium were not observed in the HPLC charts (FIGS. 18B, C).

On the other hand, the same pattern as that of the supernatant of the NS cell line culture was observed in the HPLC chart of the sample obtained by the destruction of the NS cell line itself followed by the extraction.

It can be concluded from these results that AIF is a material produced only from the NS cell line and released in culture medium.

(7) Examination of the Physico-chemical Properties of AIF and the Structural Determination The existence of amino acids or hexose in AIF finally separated and purified by HPLC was examined by the orcinol sulfate reaction or the ninhydrin reaction. Furthermore, it was found that AIF is a nucleic acid type material, since the maximum absorption of the UV spectrum is observed at near 260 nm. The molecular weight was estimated with a mass spectrometer (FAB-MASS). The structure was finally determined by the proton nuclear magnetic resonance (NMR) method.

It was suggested that respective active peaks (1–6) separated by HPLC are heat-resistant, negative to the ninhydrin and orcinol reactions, and thus comprise non-proteinous and non-hexose materials.

It was also found that AIF is a nucleic acid type material, since the maximum absorption of the UV spectrum is observed at near 260 nm (Left upper panels in FIGS. 7–12).

As the direction of the structural analysis was decided, the NS cell was cultured in a large amount (about 300), and the samples were prepared from an aliquot of each of the peaks (1–6) finally separated and purified by HPLC. The structure of the samples was finally determined by mass spectrometry (FAB-MASS) and nuclear magnetic resonace (NMR) methods. The active peaks 1–6 of AIF were 2'-deoxyuridine for P1, ribothymidine for P2, 2'-O-methyluridine for P3, thymidine for P4, 2'-O-methylinosine for P5, and 2'-O-methylguanosine for P6 (right upper panel of FIGS. 7–12).

In this connection, the molecular weight (+H) of each of the active peaks (1–6) of AIF is denoted below the arrow in mass spectrum (lower panels of FIGS. 7–12).

[II] Animal Test

There were used the typical blood cancer cell Molt4 and the typical epithelial cancer cell GCIY, on both of which the effect of AIF was experimentally confirmed in vitro. (1) About $10_8$of human stomach cancer cell (GCIY) was inoculated on 20 SCID mice, and these mice were divided into 4 groups when the diameter of tumor reached 0.5 cm (0.25 cm$^2$)(after ca. 2 weeks) to start the therapeutic experiments of tumor carrying mice with AIF. Each group comprises 5 mice.

Test Example 1

To each of 5 mice was administered a solution of the sample (TLC-B fraction) which was fractionated by TLC described above and contains six nucleosides (AIF) in phosphate buffer (PBS). A dose was 1 mg (corresponding to 90 μg of 2'-deoxyuridine, 110 μg of ribothymidine, 135 μg of 2'-O-methyluridine, 322 μg of thymidine, 226 μg of 2'-O-methylinosine, and 117 μg of 2'-O-methylguanosine) in 0.5 ml of PBS, and the sample solution was administered intravenously (through tail vein)18 times in total.

Figure 22:
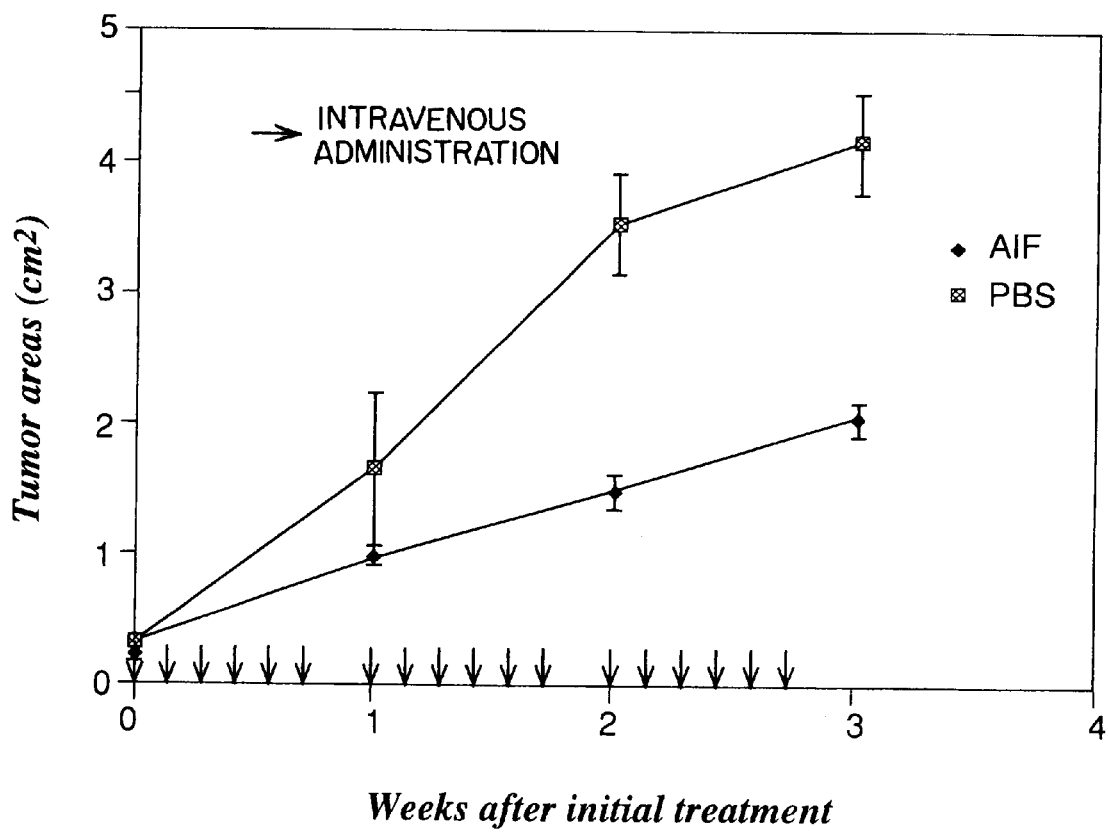
FIG. 22 is the graph which exhibits the suppressive effect of AIF on human stomach cancer cell, FIG. 23 are the photographs which show the effect of AIF on the disassimilation of human stomach cancer tissue (A, B), and the photograph which shows the result of the DNA fragmentation test (C)

As the control, the sample (TLC-A fraction) which was fractionated by TLC described above and contains the fraction lower than phenol red on TLC, that is, contains none of six nucleosides was used. It was administered intravenously (through tail vein) 18 times in total as well. The size of tumor was measured by the product of major axis and minor axis (area). FIG. 22 illustrates the mean tumor size in five mice, respectively, after 1, 2 and 3 weeks. As is obvious from the graph, significant difference was recognized between the AIF administered group and the control group, and the AIF administered group exhibited significantly stronger tumor suppressive effect compared to the control group (t test, P<0.01).

Test Example 2

Figure 23A:

A solution of 1 mg of each of the fractions TLC-A and B in 0.3 ml of PBS was directly administered in three portions (0.1 ml/dose) into tumor of 5 tumor carrying mice for 3 days. The sample containing 6 nucleosides (AIF) of the fraction TLC-B (comprising the same constituents as in Experiment 1) resulted in the complete degeneration of tumor. In the fraction TLC-A containing no AIF as the control, the degeneration of tumor could not be induced at all (as a typical example, a control tumor carrying mouse, a treated mouse, 3 AIF administered mice having tumor excised therefrom, and 3 control mice are shown in FIGS. 23A and B). As is obvious from the mechanism of the degeneration of tumor by AIF shown in FIG. 23C, AIF induced the fragmentation of DNA, that is, the tumor death due to apoptosis.

(2) About $10^8$ of human T-cell leukemia cell (Molt 4) was inoculated into 10 SCID mice, and these mice were divided into 2 groups when the diameter of tumor reached 0.3 cm (0.09 $cm^2$)(after ca. 2 weeks) to start the therapeutic experiments of tumor carrying mice with AIF.

Figure 24:
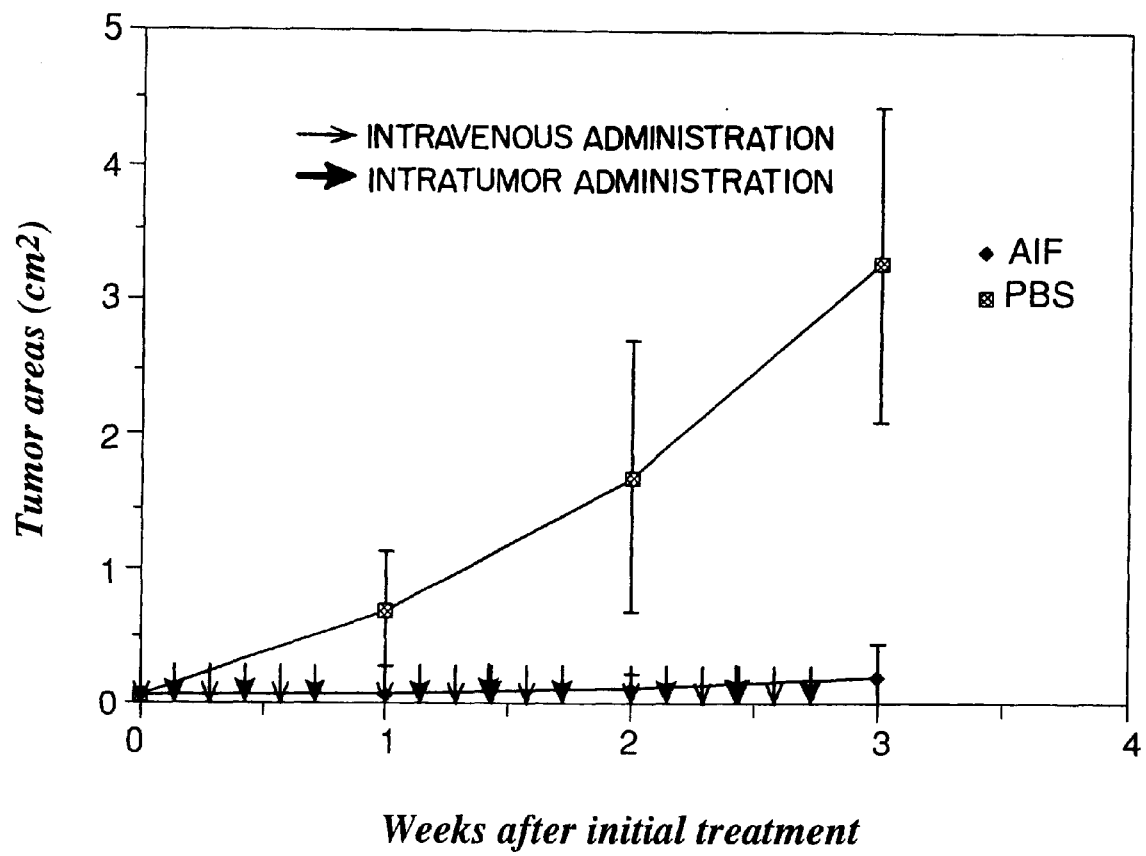
FIG. 24 is the graph which exhibits the suppressive effect of AIF on human T cell leukemia cells.

To each of 5 mice was repeatedly administered in 18 alternate intravenous and direct intratumoral administrations a solution of the three AIF nucleoside containing sample (400 μg of 2'-deoxyuridine, ribothymidine and thymidine, respectively, 1.2 mg in total) in 0.5 ml of PBS (21.6 mg in total) The size of tumor was measured by the product of major axis and minor axis (area) and monitored for 3 weeks. The tumors in the three mice among five mice were completely degenerated; and the ones in the remaining two mice were also degenerated to an extremely small size. The graph in FIG. 24 illustrates the mean tumor size in five mice, respectively, after 1, 2 and 3 weeks. As is obvious from the graph of the control group, tumor grew larger in the PBS administered control group, and thus completely significant difference was recognized between the AIF administered group and the control group (t test, P<0.001).

[III] Discussion

Maternal immune reaction on fetus is primarily controlled by decidual tissue.

It has been clarified by the investigation by the present inventors that a large number of cell groups which are conceivably LGL cell having NK cell marker are accumulated on the decidua of mammals including human at the initial stage of pregnancy. In addition, these NK cell groups is believed to play an important role in a phase of the implantation of blastocyte. That is to say, the NK cell controls the formation of fetal placenta proliferating continuously and thus being on the way of generation on pregnancy. In other words, natural immune reaction against cancer is performed in the stage of pregnancy.

The NS cell line of the present inventors is a CD57-positive HLA-DR strongly positive human natural suppressor cell which has been cloned and established from the decidual layer of human 3-month pregnant. The cell line has no estrogen or progesterone receptors which is characteristic to decidual interstitial cells or secretes no prolactin, so that it is believed a cell line floating from bone marrow or lymphatic tissues.

As the specific function of the NS cell, there have been reported not only the suppression of antibody production and lymphocyte division caused by MLR or mitogen irritation, but also the suppression of proliferation of cancer cells (Sugiura, K., M. Inaba, H. Ogata, R. Yasumuzu, E. E. Sardina, K. Inaba, S. Kuma, R. A. Good, and S. Ikehara, 1990, Inhibition of tumor cell proliferation by natural suppressor cells present in murine bone marrow, Cancer Res., 50:2582). As the effector materials of the NS cell which mediates the control of cell division, there have been indicated a protein of TGF-β family (Clark, D. A., K. C. Flanders, D. Banwatt, W. Millar-Book, J. Manuel, J. Stedronska-Clark, and B. Rowley, 1990, Murine pregnancy decidua produces a unique immunosuppressive molecule related to transforming growth factor beta-2, J. Immunol., 144:3008), and a lipid-like substance having a molecular weight of 10,000 or less (Mortari, F. and S. K. Singhal, 1988, Production of human bone marrow-derived suppressor factor. Effect on antibody synthesis and lectin-activated cell proliferation, J. Immunol., 141:3037), but their entities remained ambiguous. Also, as indicated in our previous investigation on the immuno-supressive mechanism by the NS cell (Tatsumi, K., T., Mori, E. Mori, H. Kanzaki, and T. Mori, 1987, Immunoregulatory factor released form a cell line derivative from human decidual tussue, Am. J. Reprod. Immunol. Microbiol., 13:87), a proteinic material suppresses the T cell division via IL-2.

It has been extraordinarily found that the NS cell line induces cell death due to its apoptosis (DNA fragmentation) of not only human blood cancer cells K562, Molt4 and U937, but also human stomach cancer cell GCIY and human choriocarcinoma cell BeWo, and suppresses their proliferation.

Furthermore, the substances (AIF) for inducing the apoptosis of cancer cells were separated from the supernatant of this cell line culture, and purified, and their structures were determined. The process first comprises eluting the material that the lyophilized sample of the supernatant of the NS cell line culture was hydrophobically bonded to a C18 column with acetonitrile. Active factors eluted were crude-purified by TLC. The active fraction showed a larger Rf than phenol red and suppressed the division of the K562 and Molt4 cells thus causing the DNA fragmentation. Finally, the active molecules were separated and purified as the six main peaks by HPLC on a C18 reverse column. All of the samples obtained from these six peaks suppressed the proliferation of the target cancer cells and induced the DNA fragmentation. Thus, these samples were successfully confirmed to be the original objects, i.e. AIFs. It has been also found that these six AIFs are most effective when these factors are used as an cocktail by mixing these factors (combination of plural agents currently used in chemotherapy of cancer; natural combination of plural agents in this case). In addition, these six AIFs have physicochemical properties of being negative to the orcinol reaction and ninhydrin reaction, and thus these factors were non-proteinic, hexose-free substances. These substances were estimated to have a molecular weight of 100–500 on the basis of their passing through a 500 Dalton cut dialysis membrane and their MS measurements.

Furthermore, as shown in the left upper portion of FIGS. 7–12, each of the active peaks fractionated by HPLC showed the UV spectrum having the maximum absorption at 245 nm–265 nm. That is to say, it is strongly suggested that AIF is a substance relating to nucleic acids or their derivatives.

AIF was finally separated and purified from the supernatant of a large amount of the NS cell culture to prepare a sample sufficient to the structural analysis and to finally determine its molecular weight by FAB-MASS and its structure by proton NMR (FIGS. 1–12). These six AIFs belonged to nucleosides having a unique structure in which a portion of the base or ribose is deoxygenated or methylated.

It has been found for the first time in the world so far as we know that as is the present invention, the human NS cell secretes a series of nucleic acid type substances and induces the apoptosis of cancer cells.

Clinically available nucleic acid type anti-cancer agents and anti-virus agents such as 5-FU, Futraful (FT), Furtulon, AZT, DDI and Ara-c have strong cellular toxicities, and thus constitute a social problem due to their strong side effects on administration to human bodies as well as their efficacies.

Figure 23B:
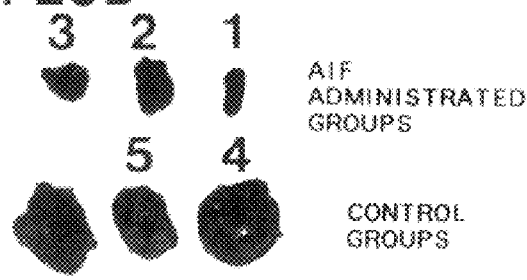
Figure 23C:
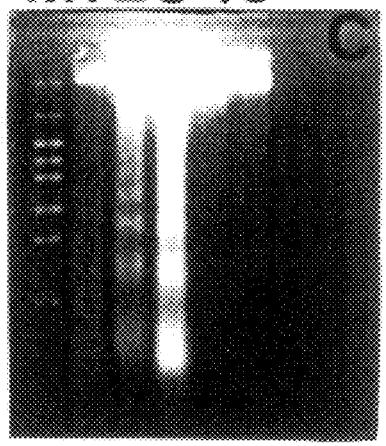

The observations on AIFs discovered by the present inventors are those of in vitro and animal experiments (these experimental systems are the usual in vitro and animal experimental systems established in the art for evaluating anti-cancer agents and anti-virus agents for human recipients; see for example FIGS. 22, 23, 24). However, there has been thereby developed a foundation for the development of ideal natural type carcinostatic agents which will not impair human normal cell at all but bring about cancer cell death through the natural pharmacological mechanism, that is, the induction of apoptosis (DNA fragmentation) specific to cancer cells while side effects are intended to be reduced on administration to human body in future.

[IV] Supplementary Descriptions of the Drawings

FIG. 14: shows the fact that the NS cell line induces the cell death of the target cancer cell due to apoptosis, but not the cell death of normal cell due to apoptosis.

As a result of direct interaction (co-culture) between the NS cell and the target cells, cell DNA was extracted and subjected to electrophoresis on 2% agarose gel.

As shown in FIG. 14A, lanes 1, 2 and 3 show the results of the co-cultures with $10^4$, $10^5$ and $10^6$/well of the NS cell, respectively, and $10^6$/well of Molt4, and the degree of the DNA fragmentation in the target cell was increased depending on the numbers of the NS cell inoculated. On the other hand, lane 5 is the result of the culture with $10^6$/well of Molt4 solely, and lane 4 is the result of the culture with $10^6$/well of NS solely. In these cases, no DNA fragmentation was observed. M is a marker.

As shown in FIG. 14B, lanes 1, 2 and 3 show the results of the co-cultures with $10^4$, $10^5$ and $10^6$/well of the NS cell, respectively, and $10^6$/well of K562, and the degree of the DNA fragmentation in the target cell was increased depending on the numbers of the NS cell inoculated. On the other hand, lane 4 is the result of the culture with $10^6$/well of K562 solely, and lane 5 is the result of the culture with $10^6$/well of the NS cell solely. In these cases, no DNA fragmentation was observed. M is a marker.

As shown in FIG. 14C, lanes 1, 2 and 3 show the results of the co-cultures with $10^6$, $10^5$ and $10^4$/well of the K562 cell and the Molt4 cell, respectively, lane 4 shows the result of culture with $10^6$/well of Molt4 solely, and lane 5 with $10^6$/well of K562 solely. In neither cases, DNA fragmentation was induced. M is a marker.

As shown in FIG. 14D, lanes 1, 2 and 3 show the results of the co-cultures with $10^4$, $10^5$ and $10^6$/well of the NS cell, respectively, and $10^6$/well of BeWo, and the degree of the DNA fragmentation in the target cell was increased depending on the numbers of the NS cell inoculated. on the other hand, lane 4 is the result of culture with $10^6$/well of NS solely, lane 5 is the result of culture with $10^6$/well of BeWo solely, lane 6 is the result of co-culture with $10^6$/well of BeWo and $10^6$/well of GCIY, and lane 7 is the result with $10^6$/well of GCIY solely. In neither cases, DNA fragmentation was observed. As shown in FIG. 14E, lanes 1, 2 and 3 show the results of the co-cultures with $10^3$, $10^4$, $10^5$ and $10^6$/well of the NS cell, respectively, and $10^6$/well of U937, and the degree of the DNA fragmentation in the target cell was increased depending on the numbers of the NS cell inoculated. On the other hand, lane 7 is the result of co-culture with $10^6$/well of Molt4 and $10^6$/well of U937, lane 8 is the result of culture with $10^6$/well of Molt4 solely, lane 6 with $10^6$/well of U937 solely, and lane 5 with $10^6$/well of NS. In neither cases, DNA fragmentation was induced. M is a marker.

As shown in FIG. 14F, lanes 1, 2 and 3 show the results of the co-cultures with $10^4$, $10^5$ and $10^6$/well of the NS cell, respectively, and $10^6$/well of GCIY, and the degree of the DNA fragmentation in the target cell was increased depending on the numbers of the NS cell inoculated. On the other hand, lane 4 is the result of culture with $10^6$/well of GCIY solely, and lane 5 is the result of culture with $10^6$/well of NS solely. In neither cases, DNA fragmentation was observed. M is a marker.

As shown in FIG. 14G, lanes 1, 2 and 3 show the results of the co-cultures with $10^4$, $10^5$ and $10^6$/well of the NS cell, respectively, and $10^6$/well of WI-38, and no DNA fragmentation in the target cell was observed notwithstanding the increased numbers of the NS cell. Lane 4 is the result of culture with $10^6$/well of WI-38 solely, and lane 4 is the result of culture with $10^6$/well of NS solely. In neither cases, DNA fragmentation was induced. M is a marker.

FIG. 15: It is explained that the NS cell line suppresses the proliferation of the target cell in the indirect co-culture with the K562/Molt4 cells.

As shown in FIG. 15, in the system of indirect interaction (indirect co-culture) in which the NS cell and the target K562/Molt4 cells are placed in a chamber, the number of the target cancer cells within the chamber was decreased along with the increase of the number of the NS cell after 72 hours.

Figure 16:
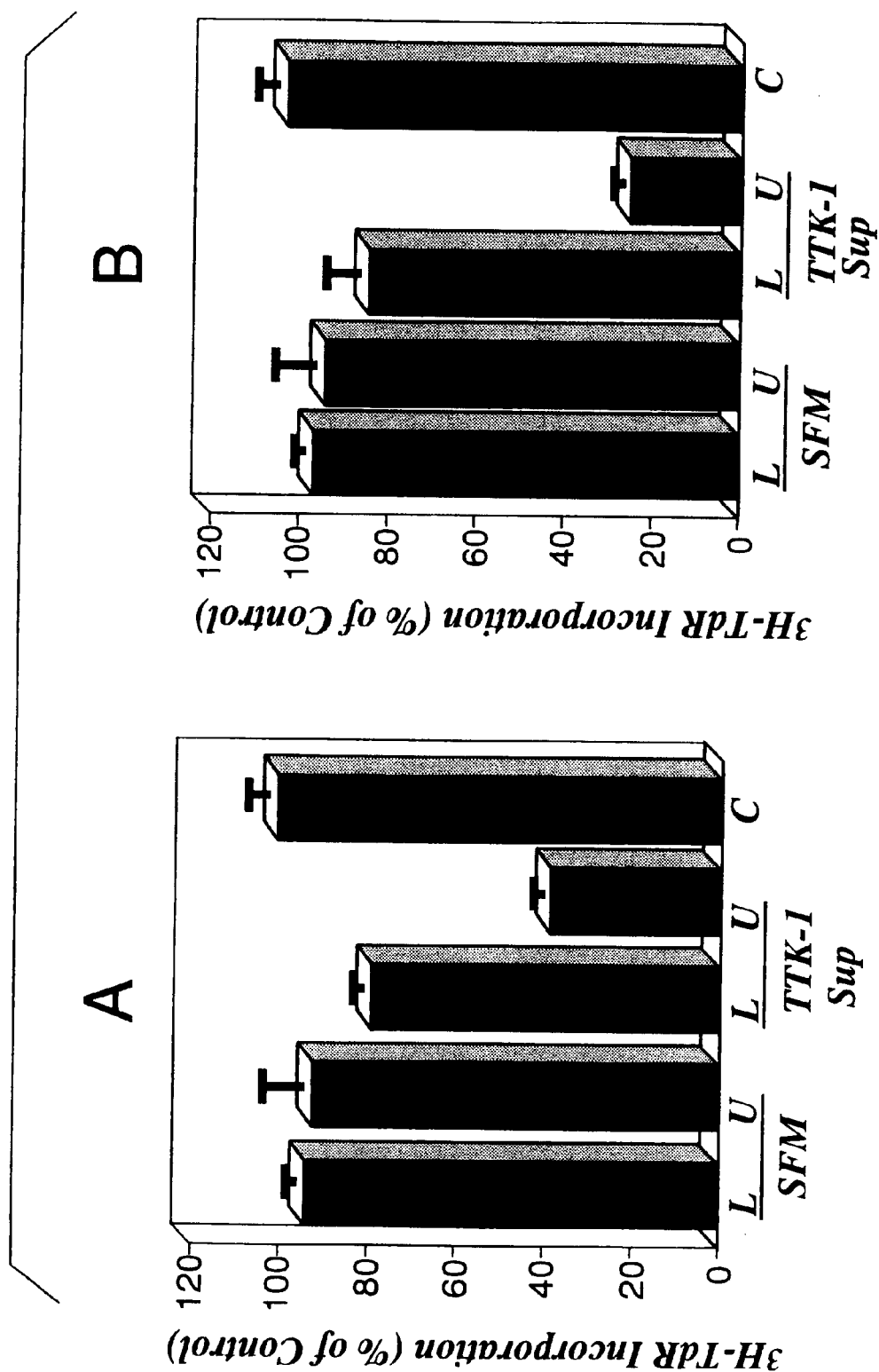
Figure 17:
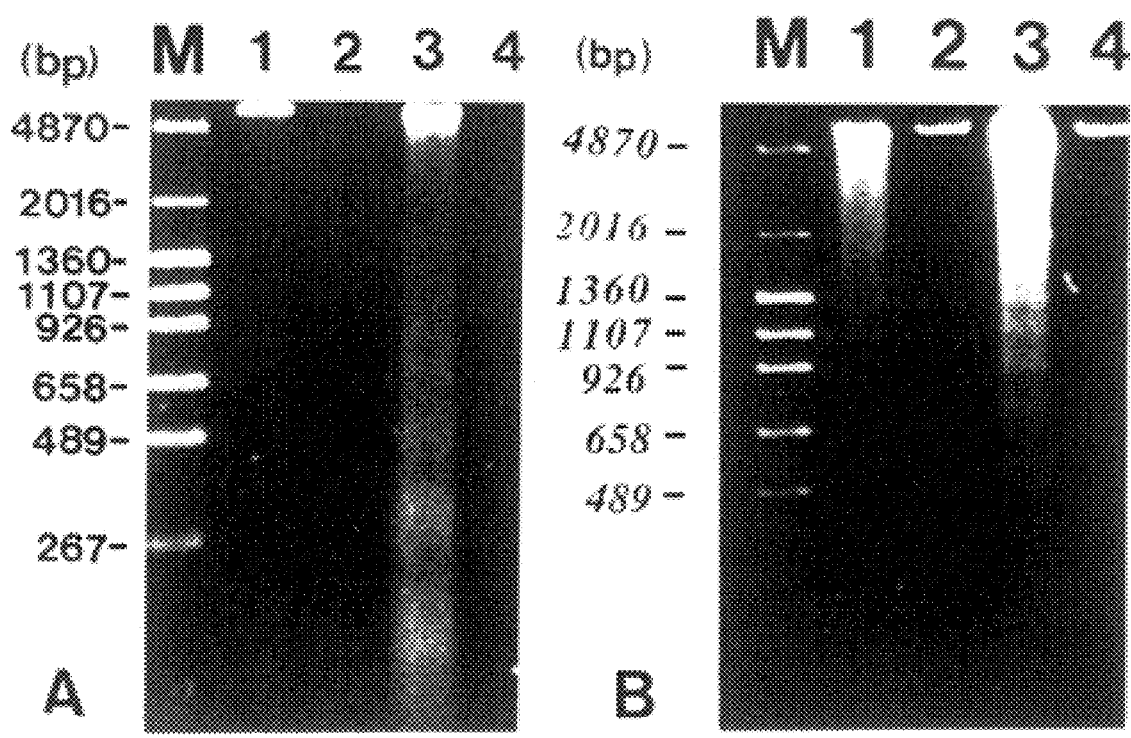

FIGS. 16–17: It is explained that AIF crude-purified by thin layer chromatography (TLC) suppresses the $^3$H-thymidine incorporation into the target cell and induces DNA fragmentation.

A fraction obtained by applying a sample lyophilized from about 50 ml of the supernatant (TTK-1 Sup) of the NS (TTK-1) cell culture to a C18 column and eluting the fraction retained in the column with acetonitrile and concentrating the elute suppressed the division of the K562/Molt4 cells.

This fraction was further applied to TLC as shown in FIG. 16A in order to obtain a fraction (U) upper than phenol red (Rf 0.5) contained in the medium on TLC. This fraction (U) was recognized to suppress the division of the K562 cell as compared to serum free medium (SFM), the control group (C) and a fraction (L) lower than the phenol red on TLC.

On the other hand, this fraction was further applied to TLC as shown in FIG. 16B in order to obtain a fraction (U) upper than phenol red (Rf 0.5) contained in the medium on TLC. This fraction (U) was recognized to significantly suppress the division of the Molt4 cell as compared to a fraction (L) lower than the phenol red on TLC.

In the control group (C) and the fresh serum free medium (SFM) used, no suppression of the proliferation of the target cells.

As illustrated in FIGS. 17A and B, a fraction obtained by applying a sample lyophilized from about 50 ml of the supernatant of the NS (TTK-1) cell culture to a C18 column and eluting the fraction retained in the column with acetonitrile and concentrating the elute. The fraction thus obtained was applied to TLC and separated into the fraction (U, lanes 1 and 3) upper than phenol red (Rf 0.5) contained in the medium and the fraction (L, lanes 2 and 4) lower than phenol red, each of which fractions was examined for the existence of a substance which induces the DNA fragmentation of the K562/Molt4 cells. These extracts were reacted with the K562/Molt4 cells, and cell DNA was extracted after 24 hours (lane 1 and 2), 48 hours (lane 3 and 4), and subjected to electrophoresis on 2% agarose gel. As shown in the figure, the substance (AIF) which induces the apoptosis (cell death) of human cancer cells is produced in the supernatant of the NS cell culture, and AIF is found in the fraction which moves more rapidly than phenol red on TLC (Rf>0.5).

Figure 18:
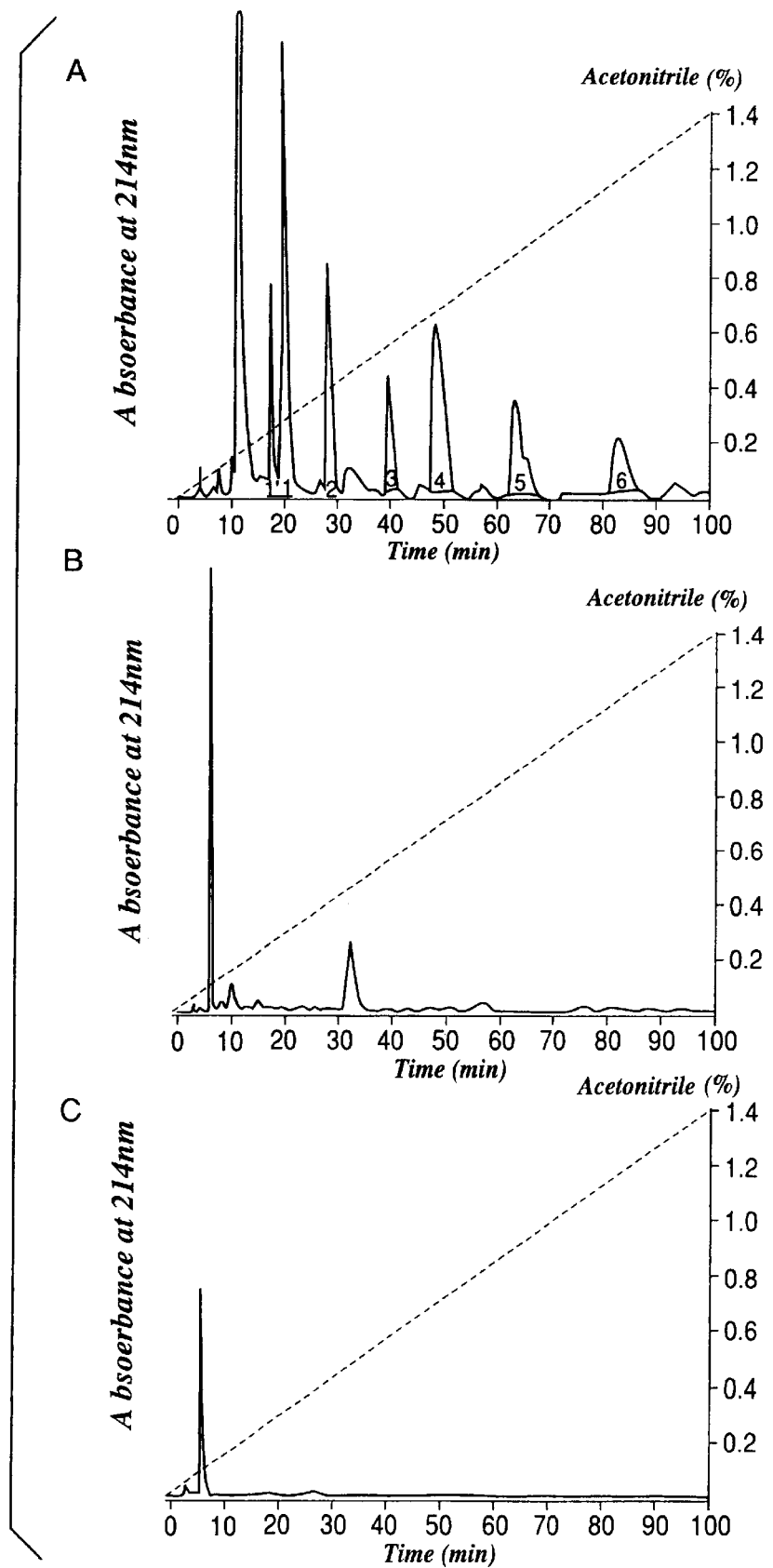
Figure 19:
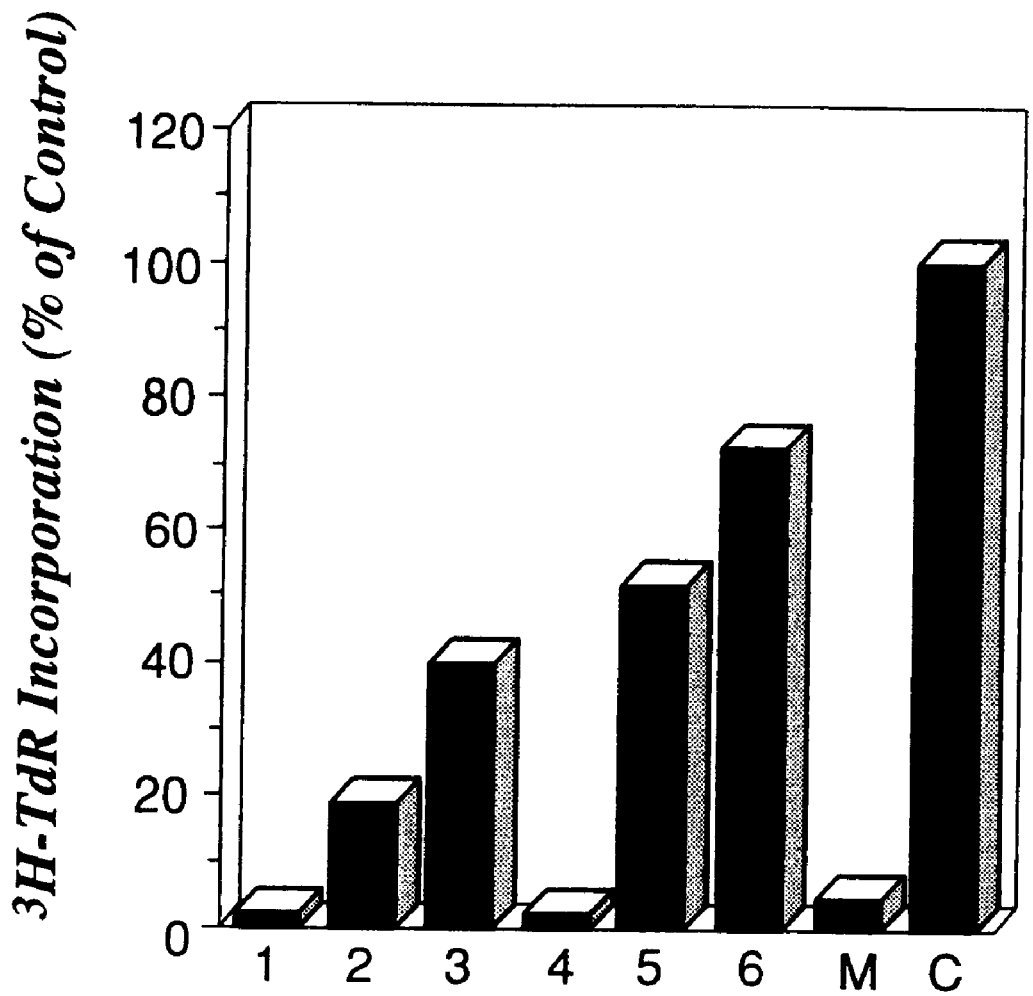

FIG. 18: HPLC chart of AIF finally separated by HPLC

As shown in FIG. 18A, the total active fraction crude-purified by TLC from 500 ml of the supernatant of the NS (TTK-1) culture was separated and extracted by reverse-phase HPLC on a TSK gel ODS-80™ (Tosoh). Six main peaks (1–6) were obtained.

As shown in FIGS. 18B and C, when the supernatant (B) of Molt4 cell culture or a fresh medium (C) was subjected to the same treatment as that of the NS (TTK-1) cell culture medium and finally applied to HPLC, none of such active peaks obtained from the NS cell culture medium (1–6) were observed in the HPLC chart.

Figure 20:
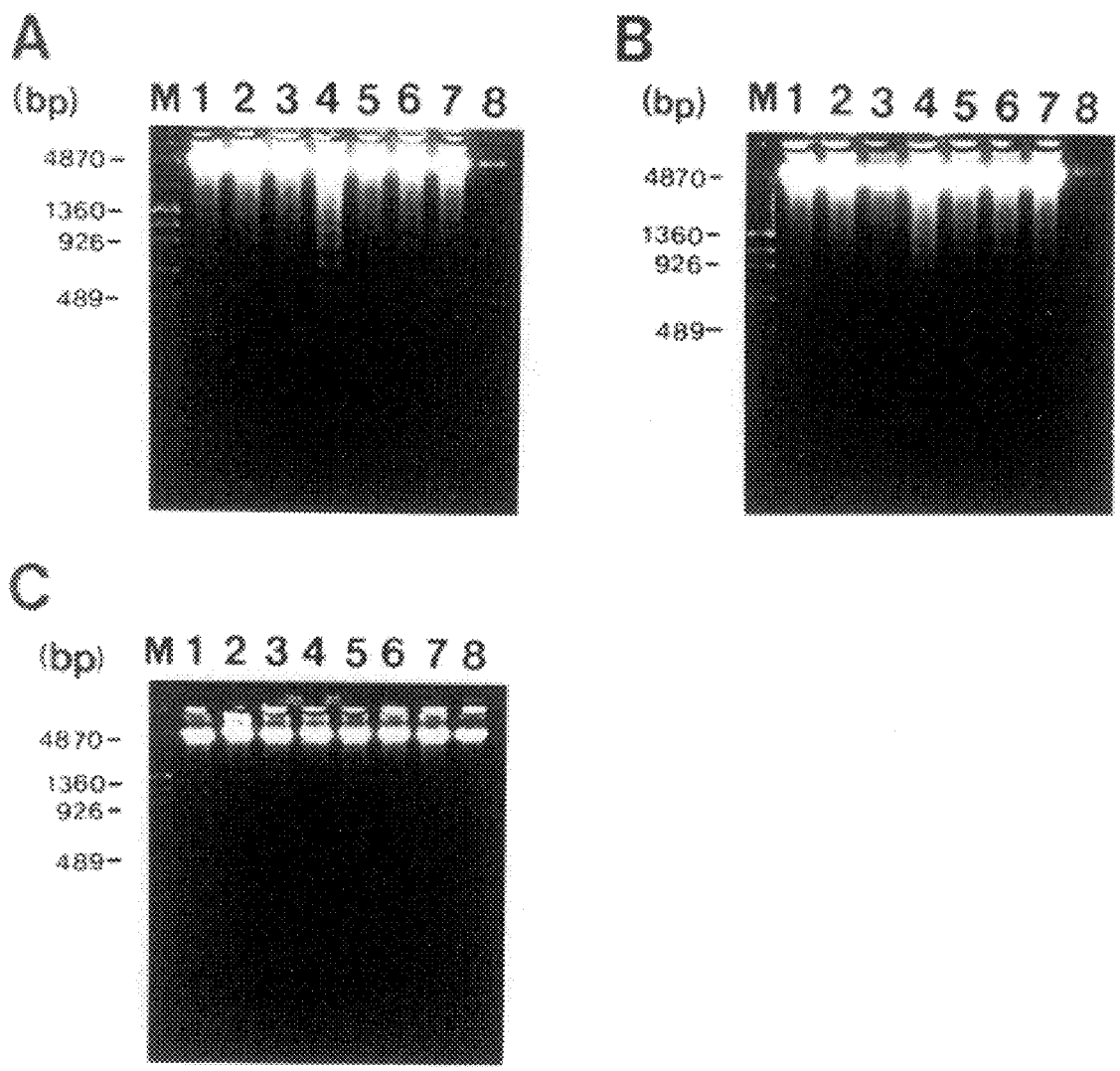

FIGS. 19 and 20: There is explained the fact that AIF finally separated by HPLC suppresses the incorporation of $^3$H-thymidine into the target cancer cell and induces the DNA fragmentation, and the critical amount of AIF which can induce the fragmentation.

As shown in FIG. 19, all of the samples (7 µg/ml) from the main peaks (1–6) separated by HPLC suppressed the incorporation of $^3$H-thymidine into the Molt4 cell. In particular, the samples from the peaks 1 and 2 exhibited strong activity, and 1/10 dilution of the mixed sample of these peaks (0.7 µg/ml, respectively) also exhibited strong activity. As shown in the column M of FIG. 19, this indicates the synergistic effect of these peaks.

As shown in FIG. 20A, samples prepared from the respective peaks (1–6) were reacted with the Molt4 cell for 48 hours, and then the DNA of the Molt4 cell was extracted and subjected to electrophoresis on 2% agarose gel. Corresponding to the Molt4 cell division suppressive effect of respective active peaks (1–6), both of the samples derived from the respective peaks (1–6) and the mixture of the 1/10 dilutions of respective peaks (1–6) induced the DNA fragmentation of the Molt4 cell (FIG. 20A, lanes 1–7).

As shown in FIGS. 20B and C, samples derived from the respective active peaks (1–6) separated by HPLC (B: $7 \times 3^{-2}$ µg/ml, C: $7 \times 3^{-5}$ µg/ml) were reacted with the Molt4 cell for 48 hours, and then the DNA of the Molt4 cell was extracted and subjected to electrophoresis on 2% agarose gel. As shown in FIG. 20B, in the samples derived from the respective peaks (1–6) ($7 \times 3^{-2}$ µg/ml) and the mixture of the 1/10 dilutions of respective peaks (1–6) ($0.7 \times 3^{-2}$ µg/ml), the DNA fragmentation of the Molt4 cell was observed, but the effect disappeared at a low concentration of $7 \times 3^{-5}$ µg/ml of each sample alone or of $0.7 \times 3^{-5}$ µg/ml of the mixture of the 1/10 dilutions as shown in FIG. 20C (lanes 1–7).

Figure 21:
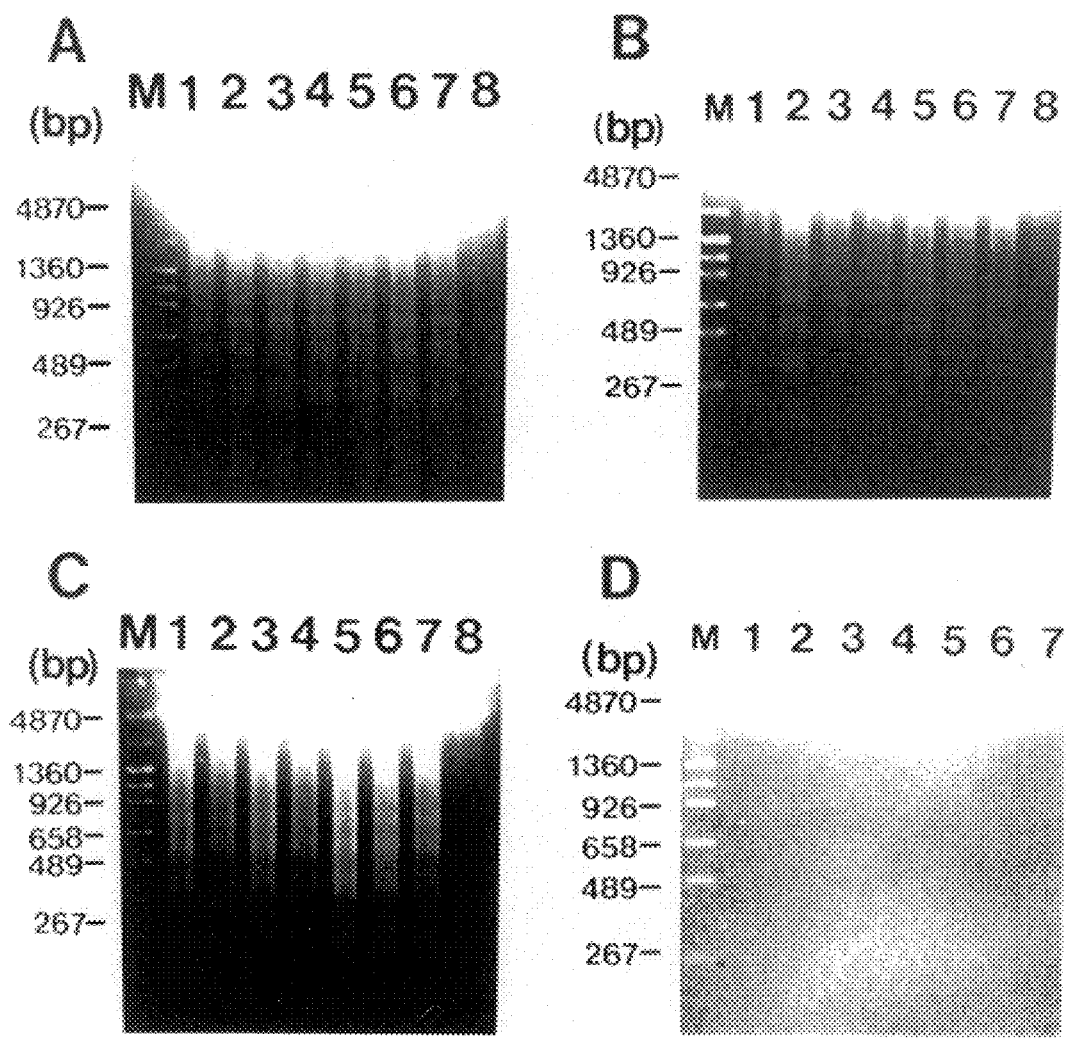

FIG. 21: It is explained that AIF finally separated by HPLC induces the DNA fragmentation of the human cancer cells BeWo/U937/GCIY, but not of the human normal cell WI-38.

As shown in FIGS. 21A, B and C, samples derived from the respective peaks (1–6) (21 µg/ml) and the mixture of the 1/10 dilutions of samples derived from respective peaks (1–6) (2.1 µg/ml) were reacted with the BeWo (A)/U937 (B)/GCIY (C) cells for 48 hours, and then the DNA of each target cell was extracted and subjected to electrophoresis on 2% agarose gel. Corresponding to the target cell division suppressive effect of respective active peaks (1–6), both of the samples derived from the respective peaks (1–6) and the mixture of the 1/10 dilutions of respective peaks (1–6) induced the DNA fragmentation of the target cell (lanes 1–7).

As shown in FIG. 21D, samples derived from the respective peaks (1–6) in a 3-time amount (63 µg/ml) of that used for the target cancer cell were reacted with the human normal cell WI-38 for 48 hours, and then the DNA of the WI-38 cell was extracted and subjected to electrophoresis on 2% agarose gel. None of the samples derived from the active peaks caused the suppression of the division or DNA fragmentation of the normal cell.

FIGS. 7–12: Physicochemical properties and structural determination of the respective active peaks 1–6 (AIF) separated by HPLC The NS cell line was cultured in a large amount (ca. 300 L), and samples fractionated from the respective peaks (1–6) separated and purified by HPLC were prepared.

As shown in the left upper panels of P1–P6 in FIGS. 7–12, respectively, it was found from the observation of the maximum absorption at about 260 nm in UV spectrum analysis that AIF is a nucleic acid type substance.

As the direction of the structural analysis was decided by the UV spectrum analysis, the molecular weight was determined by the mass spectrometry (FAB-MASS) (arrows in lower panels). Furthermore, the structure of AIFs was finally determined by the nuclear magnetic resonance (NMR) method as shown in FIGS. 7–12 (right upper).

EXAMPLES

The present invention is now described in more detail with reference to examples, but it is not limited to these examples.

Example 1

Description of Culture Medium and Culture Liquid

The supernatant of the NS cell culture (500 ml) after culture for 3 days under the condition of 5% $CO_2$ and 37° C. was lyophilized and separated through a C18 column. As the active substances were bonded to the column, these substances were separated and eluted with acetonitrile and methanol. The solvent was evaporated with nitrogen gas, and the elute was concentrated to dryness.

The solution of the substance separated with the C18 column in chloroform: methanol (1:1) was spotted on a thin layer (Kieselgel) and developed with chloroform: methanol: distilled water (60:40:8). After development, the plate was divided into the fraction lower than the band of the phenol red reagent (L) and the one upper than the band (U), the gel was scratched off to recover the respective fractions by extraction with chloroform: methanol (1:1) and to dry the extract with nitrogen gas.

The active fraction (U) of TLC was separated and purified on an ODS-80™ column (Tosoh) by elution with acetonitrile containing 0.1% trifluoroacetic acid with a gradient of 0–5%/360 min at a flow rate of 0.5 ml/min while monitoring OD at 214 nm to give six main peaks (1–6) (FIG. 18A, HPLC chart).

The aimed products P1, P2, P3, P4, P5 and P6 were obtained in an amount of 0.014 mg, 0.017 mg, 0.021 mg, 0.050 mg, 0.035 mg and 0.018 mg, respectively.

The preparation examples of the compounds of the present invention are described below, but the preparation of the compounds of the present invention is not limited to these preparation examples.

Preparation Example 1

Present substance (P1) 10 (parts) (denoting hereinafter as by weight)

Magnesium hydrogen bicarbonate 15

Lactose 75

Ingredients listed above were blended uniformly to prepare a pulverized or granular powder having a particle size of 350 µm or less. The powder was charged in a capsule container to form a capsule.

25

Preparation Example 2

Present substance (P2) 45 (parts)
Starch 15
Lactose 16
Crystalline cellulose 21
Polyvinyl alcohol 3
Distilled water 30

After uniformly blending the ingredients listed above, the blend was crushed into granules which were dried and then sieved to form granule having a particle size of 177–1410 μm.

Preparation Example 3

After preparing granule in the same manner as in Preparation Example 2, 4 parts of calcium stearate was added to 96 parts of the granule, and the mixture was compression molded to prepare tablet having a diameter of 10 mm.

Preparation Example 4

To 90 parts of the granule prepared by the method described in Preparation Example 2 was added 10 parts of crystalline cellulose and 3 parts of calcium stearate, and the mixture was compression molded to form tablet having a diameter of 8 mm, to which a syrup gelatin/precipitated calcium carbonate suspension was added to prepare dragée.

Preparation Example 5

Present substance (P3) 0.6 (parts)
Nonionic surface active agent 2.4
Physiological saline 97

After blending with warming the ingredients listed above, the blend was charged into an ampoule, and sterilized to prepare injection.

INDUSTRIAL APPLICABILITY

The compounds of the present invention represented by the formula (I) or a pharmaceutically acceptable salts thereof impair none of human normal cells, and when administered to human body, it is expected to treat human diseases such as carcinoma and viral conditions by the natural mechanism that it acts specifically on cancer cells to cause cancer cell death due to apoptosis while planning the reduction of its side effects. Thus, the compounds of the present invention are useful as anti-tumor agent or anti-virus agent in the art of pharmaceuticals.

What is claimed is:

1. A process for preparing the anti-tumor or anti-viral substance represented by the following formula (1), or a pharmaceutically acceptable salt thereof, wherein human placental decidua derived cells having the ability of producing the substance are cultured, the compound is harvested from the culture, and optionally converted into a pharmaceutically acceptable salt thereof, in which the human placental decidua derived cells are human type natural suppressor cells having cell surface markers as positive CD57 and bright HLA.DR in the cell line deposited with the acceptance number of FERM BP-6350:

26

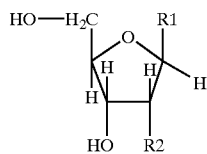

wherein

R1 represents the group

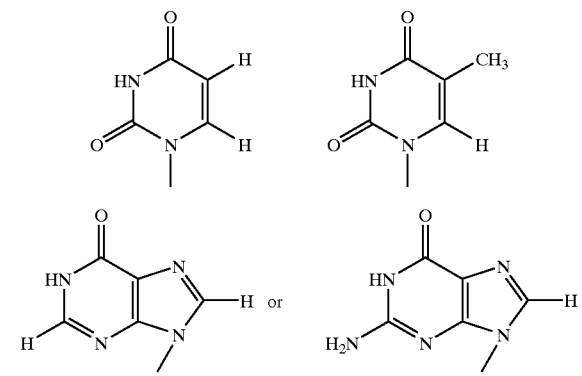

R2 represents a hydrogen atom, a hydroxy group or a methoxy group, or a pharmaceutically acceptable salt thereof.

2. The process according to claim 1, wherein R1 and R2 in formula (1), respectively represent

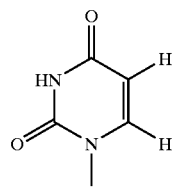

and a hydrogen atom,

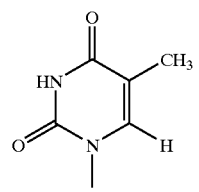

and a hydroxy group,

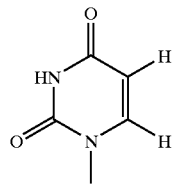

and a methoxy group,

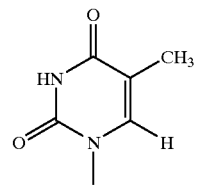 and a hydrogen atom,

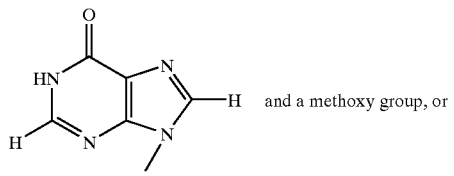 and a methoxy group, or

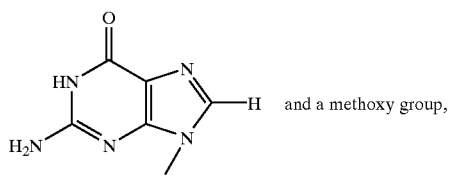 and a methoxy group, or a pharmaceutically acceptable salt thereof.

3. A process for suppressing tumor or virus, wherein an effective amount of the anti-tumor or anti-viral substance represented by formula (1) of claim 1 or a pharmaceutically acceptable salt thereof is administered to a patient who requires the suppression of tumor or virus.

4. The process according to claim 3, wherein R1 and R2 in formula (1), respectively represent

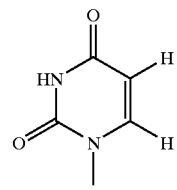 and a hydrogen atom,

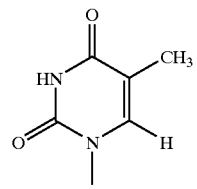 and a hydroxy group,

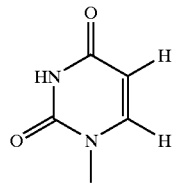 and a methoxy group,

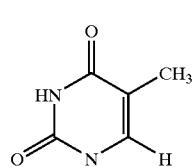 and a hydrogen atom,

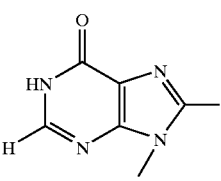 and a methoxy group, or

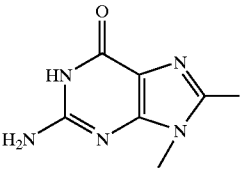 and a methoxy group, or a pharmaceutically acceptable salt thereof.

* * * * *